(12) United States Patent
Lomeli et al.

(10) Patent No.: US 12,303,341 B2
(45) Date of Patent: **\*May 20, 2025**

(54) CAMERA POSITION INDICATION SYSTEMS AND METHODS

(71) Applicant: Medos International Sarl, Le Locle (CH)

(72) Inventors: Roman Lomeli, Plymouth, MA (US); Eric Buehlmann, Duxbury, MA (US); James Paiva, Warren, RI (US); Leonard Bryant Guffey, Duxbury, MA (US)

(73) Assignee: Medos International Srl, Le Locle (CH)

( * ) Notice: Subject to any disclaimer, the term of this patent is extended or adjusted under 35 U.S.C. 154(b) by 0 days.

This patent is subject to a terminal disclaimer.

(21) Appl. No.: 18/456,988

(22) Filed: Aug. 28, 2023

(65) Prior Publication Data

US 2024/0058090 A1 Feb. 22, 2024

Related U.S. Application Data

(63) Continuation of application No. 17/200,750, filed on Mar. 12, 2021, now Pat. No. 11,771,517.

(51) Int. Cl.
*A61B 90/00* (2016.01)
*G06F 3/14* (2006.01)
(Continued)

(52) U.S. Cl.
CPC ............ *A61B 90/361* (2016.02); *A61B 90/37* (2016.02); *G06F 3/1423* (2013.01); *G06T 11/00* (2013.01);
(Continued)

(58) Field of Classification Search
CPC . A61B 90/361; A61B 90/37; A61B 2090/365; H04N 23/66; H04N 23/695;
(Continued)

(56) References Cited

U.S. PATENT DOCUMENTS

| 4,573,448 A | 3/1986 | Kambin |
| 4,646,738 A | 3/1987 | Trott |

(Continued)

FOREIGN PATENT DOCUMENTS

| CN | 102727309 B | 11/2014 |
| DE | 9415039 U1 | 11/1994 |

(Continued)

OTHER PUBLICATIONS

International Search Report and Written Opinion for Application No. PCT/US2015/043554, mailed Nov. 19, 2015 (8 pages).

(Continued)

*Primary Examiner* — Michelle Chin
(74) *Attorney, Agent, or Firm* — Barnes & Thornburg LLP

(57) ABSTRACT

Camera position indication systems and methods are disclosed herein for conveying a camera's position to a user and/or adjusting a camera view display to match a user's perspective during a surgical procedure. In one embodiment, an example method can include receiving an output view from a camera placed within a channel of an access device to view a surgical site within a patient, receiving an input of camera position from a user, and showing on a display the output view from the camera and an indication of camera position based on the input of camera position.

22 Claims, 15 Drawing Sheets

(51) Int. Cl.
  *G06T 11/00* (2006.01)
  *H04N 5/262* (2006.01)
  *H04N 5/265* (2006.01)
  *H04N 23/695* (2023.01)
  *H04N 23/66* (2023.01)

(52) U.S. Cl.
  CPC ........... *H04N 5/2628* (2013.01); *H04N 5/265* (2013.01); *H04N 23/695* (2023.01); *A61B 2090/365* (2016.02); *G06T 2210/41* (2013.01); *H04N 23/66* (2023.01)

(58) Field of Classification Search
  CPC .... H04N 5/2628; H04N 5/265; G06F 3/1423; G06T 11/00; G06T 2210/41
  See application file for complete search history.

(56) References Cited

U.S. PATENT DOCUMENTS

| | | | |
|---|---|---|---|
| 4,678,459 A | 7/1987 | Onik et al. |
| 4,863,430 A | 9/1989 | Klyce et al. |
| 4,888,146 A | 12/1989 | Dandeneau |
| 5,080,662 A | 1/1992 | Paul |
| 5,195,541 A | 3/1993 | Obenchain |
| 5,285,795 A | 2/1994 | Ryan et al. |
| 5,395,317 A | 3/1995 | Kambin |
| 5,439,464 A | 8/1995 | Shapiro |
| 5,529,580 A | 6/1996 | Kusunoki et al. |
| 5,540,706 A | 7/1996 | Aust et al. |
| 5,569,290 A | 10/1996 | McAfee |
| 5,591,187 A | 1/1997 | Dekel |
| 5,601,569 A | 2/1997 | Pisharodi |
| 5,662,300 A | 9/1997 | Michelson |
| 5,688,222 A | 11/1997 | Hluchy et al. |
| 5,730,754 A | 3/1998 | Obenchain |
| 5,733,242 A | 3/1998 | Rayburn et al. |
| 5,735,792 A | 4/1998 | Vanden Hoek et al. |
| 5,820,623 A | 10/1998 | Ng |
| 5,885,300 A | 3/1999 | Tokuhashi et al. |
| 5,894,369 A | 4/1999 | Akiba et al. |
| 5,899,425 A | 5/1999 | Corey, Jr. et al. |
| 5,954,635 A | 9/1999 | Foley et al. |
| 6,033,105 A | 3/2000 | Barker et al. |
| 6,053,907 A | 4/2000 | Zirps |
| 6,063,021 A | 5/2000 | Hossain et al. |
| 6,110,182 A | 8/2000 | Mowlai-Ashtiani |
| 6,200,322 B1 | 3/2001 | Branch et al. |
| 6,234,961 B1 | 5/2001 | Gray |
| 6,283,966 B1 | 9/2001 | Houfburg |
| 6,286,179 B1 | 9/2001 | Byrne |
| 6,296,644 B1 | 10/2001 | Saurat et al. |
| 6,322,498 B1 | 11/2001 | Gravenstein et al. |
| 6,354,992 B1 | 3/2002 | Kato |
| 6,371,968 B1 | 4/2002 | Kogasaka et al. |
| 6,383,191 B1 | 5/2002 | Zdeblick et al. |
| 6,447,446 B1 | 9/2002 | Smith et al. |
| 6,468,289 B1 | 10/2002 | Bonutti |
| 6,558,407 B1 | 5/2003 | Ivanko et al. |
| 6,575,899 B1 | 6/2003 | Foley et al. |
| 6,579,281 B2 | 6/2003 | Palmer et al. |
| 6,626,830 B1 | 9/2003 | Califiore et al. |
| 6,648,915 B2 | 11/2003 | Sazy |
| 6,676,597 B2 | 1/2004 | Guenst et al. |
| 6,688,564 B2 | 2/2004 | Salvermoser et al. |
| 6,758,809 B2 | 7/2004 | Briscoe et al. |
| 6,808,505 B2 | 10/2004 | Kadan |
| 6,887,198 B2 | 5/2005 | Phillips et al. |
| 6,983,930 B1 | 1/2006 | La Mendola et al. |
| 7,087,058 B2 | 8/2006 | Cragg |
| 7,104,986 B2 | 9/2006 | Hovda et al. |
| 7,137,949 B2 | 11/2006 | Scirica et al. |
| 7,182,731 B2 | 2/2007 | Nguyen et al. |
| 7,341,556 B2 | 3/2008 | Shalman |
| 7,434,325 B2 | 10/2008 | Foley et al. |
| 7,591,790 B2 | 9/2009 | Pflueger |
| 7,594,888 B2 | 9/2009 | Raymond et al. |
| 7,618,431 B2 | 11/2009 | Roehm, III et al. |
| 7,636,596 B2 | 12/2009 | Solar |
| 7,637,905 B2 | 12/2009 | Saadat et al. |
| 7,641,659 B2 | 1/2010 | Emstad et al. |
| 7,771,384 B2 | 8/2010 | Ravo |
| 7,794,456 B2 | 9/2010 | Sharps et al. |
| 7,811,303 B2 | 10/2010 | Fallin et al. |
| 7,931,579 B2 | 4/2011 | Bertolero et al. |
| 7,946,981 B1 | 5/2011 | Cubb |
| 7,951,141 B2 | 5/2011 | Sharps et al. |
| 7,959,564 B2 | 6/2011 | Ritland |
| 7,988,623 B2 | 8/2011 | Pagliuca et al. |
| 8,007,492 B2 | 8/2011 | DiPoto et al. |
| 8,038,606 B2 | 10/2011 | Otawara |
| 8,043,381 B2 | 10/2011 | Hestad et al. |
| 8,062,218 B2 | 11/2011 | Sebastian et al. |
| 8,092,464 B2 | 1/2012 | McKay |
| 8,096,944 B2 | 1/2012 | Harrel |
| 8,202,216 B2 | 6/2012 | Melkent et al. |
| 8,236,006 B2 | 8/2012 | Hamada |
| 8,333,690 B2 | 12/2012 | Ikeda |
| 8,360,970 B2 | 1/2013 | Mangiardi |
| 8,372,131 B2 | 2/2013 | Hestad et al. |
| 8,382,048 B2 | 2/2013 | Nesper et al. |
| 8,397,335 B2 | 3/2013 | Gordin et al. |
| 8,435,174 B2 | 5/2013 | Cropper et al. |
| 8,460,180 B1 | 6/2013 | Zarate et al. |
| 8,460,186 B2 | 6/2013 | Ortiz et al. |
| 8,460,310 B2 | 6/2013 | Stern |
| 8,518,087 B2 | 8/2013 | Lopez et al. |
| 8,535,220 B2 | 9/2013 | Mondschein |
| 8,556,809 B2 | 10/2013 | Vijayanagar |
| 8,585,726 B2 | 11/2013 | Yoon et al. |
| 8,602,979 B2 | 12/2013 | Kitano |
| 8,622,894 B2 | 1/2014 | Banik et al. |
| 8,636,655 B1 | 1/2014 | Childs |
| 8,690,764 B2 | 4/2014 | Clark et al. |
| 8,721,536 B2 | 5/2014 | Marino et al. |
| 8,740,779 B2 | 6/2014 | Yoshida |
| 8,784,421 B2 | 7/2014 | Carrison et al. |
| 8,821,378 B2 | 9/2014 | Morgenstern Lopez et al. |
| 8,834,507 B2 | 9/2014 | Mire et al. |
| 8,845,734 B2 | 9/2014 | Weiman |
| 8,852,242 B2 | 10/2014 | Morgenstern Lopez et al. |
| 8,870,753 B2 | 10/2014 | Boulais et al. |
| 8,870,756 B2 | 10/2014 | Maurice |
| 8,876,712 B2 | 11/2014 | Yee et al. |
| 8,894,573 B2 | 11/2014 | Loftus et al. |
| 8,894,653 B2 | 11/2014 | Solsberg et al. |
| 8,926,502 B2 | 1/2015 | Levy et al. |
| 8,932,207 B2 | 1/2015 | Greenburg et al. |
| 8,932,360 B2 | 1/2015 | Womble et al. |
| 8,936,605 B2 | 1/2015 | Greenberg |
| 8,974,381 B1 | 3/2015 | Lovell et al. |
| 8,986,199 B2 | 3/2015 | Weisenburgh, II et al. |
| 8,992,580 B2 | 3/2015 | Bar et al. |
| 9,028,522 B1 | 5/2015 | Prado |
| 9,050,146 B2 | 6/2015 | Woolley et al. |
| 9,055,936 B2 | 6/2015 | Mire et al. |
| 9,072,431 B2 | 7/2015 | Adams et al. |
| 9,078,562 B2 | 7/2015 | Poll et al. |
| 9,131,948 B2 | 9/2015 | Fang et al. |
| 9,144,374 B2 | 9/2015 | Maurice, Jr. |
| 9,198,674 B2 | 12/2015 | Benson et al. |
| 9,211,059 B2 | 12/2015 | Drach et al. |
| 9,216,016 B2 | 12/2015 | Fiechter et al. |
| 9,216,125 B2 | 12/2015 | Sklar |
| 9,232,935 B2 | 1/2016 | Brand et al. |
| 9,247,997 B2 | 2/2016 | Stefanchik et al. |
| 9,265,491 B2 | 2/2016 | Lins et al. |
| 9,277,928 B2 | 3/2016 | Morgenstern Lopez |
| 9,307,972 B2 | 4/2016 | Lovell et al. |
| 9,320,419 B2 | 4/2016 | Kirma et al. |
| RE46,007 E | 5/2016 | Banik et al. |
| RE46,062 E | 7/2016 | James et al. |
| 9,386,971 B1 | 7/2016 | Casey et al. |
| 9,387,313 B2 | 7/2016 | Culbert et al. |

(56) References Cited

U.S. PATENT DOCUMENTS

| | | |
|---|---|---|
| 9,414,828 B2 | 8/2016 | Abidin et al. |
| 9,486,296 B2 | 11/2016 | Mire et al. |
| 9,492,194 B2 | 11/2016 | Morgenstern Lopez et al. |
| 9,510,853 B2 | 12/2016 | Aljuri et al. |
| 9,526,401 B2 | 12/2016 | Saadat et al. |
| 9,579,012 B2 | 2/2017 | Vazales et al. |
| 9,603,510 B2 | 3/2017 | Ammirati |
| 9,603,610 B2 | 3/2017 | Richter et al. |
| 9,610,007 B2 | 4/2017 | Kienzle et al. |
| 9,610,095 B2 | 4/2017 | To |
| 9,629,521 B2 | 4/2017 | Ratnakar |
| 9,655,605 B2 | 5/2017 | Serowski et al. |
| 9,655,639 B2 | 5/2017 | Mark |
| 9,668,643 B2 | 6/2017 | Kennedy, II et al. |
| 9,675,235 B2 | 6/2017 | Lieponis |
| 9,700,378 B2 | 7/2017 | Mowlai-Ashtiani |
| 9,706,905 B2 | 7/2017 | Levy |
| 10,758,220 B2 | 9/2020 | White et al. |
| 10,779,810 B2 | 9/2020 | Flock et al. |
| 11,771,517 B2 | 10/2023 | Lomell et al. |
| 2002/0022762 A1 | 2/2002 | Beane et al. |
| 2002/0138020 A1 | 9/2002 | Pflueger |
| 2003/0083555 A1 | 5/2003 | Hunt et al. |
| 2003/0171744 A1 | 9/2003 | Leung et al. |
| 2003/0191474 A1 | 10/2003 | Cragg et al. |
| 2004/0122446 A1 | 6/2004 | Solar |
| 2004/0127992 A1 | 7/2004 | Serhan et al. |
| 2004/0143165 A1 | 7/2004 | Alleyne |
| 2005/0085692 A1 | 4/2005 | Kiehn et al. |
| 2005/0090848 A1 | 4/2005 | Adams |
| 2005/0187570 A1 | 8/2005 | Nguyen et al. |
| 2005/0256525 A1 | 11/2005 | Culbert et al. |
| 2006/0206118 A1 | 9/2006 | Kim et al. |
| 2007/0055259 A1 | 3/2007 | Norton et al. |
| 2007/0129634 A1 | 6/2007 | Hickey et al. |
| 2007/0149975 A1 | 6/2007 | Oliver et al. |
| 2007/0203396 A1 | 8/2007 | McCutcheon et al. |
| 2007/0225556 A1 | 9/2007 | Ortiz et al. |
| 2007/0260113 A1 | 11/2007 | Otawara |
| 2008/0015621 A1 | 1/2008 | Emanuel |
| 2008/0033251 A1 | 2/2008 | Araghi |
| 2008/0081951 A1 | 4/2008 | Frasier et al. |
| 2008/0159653 A1 | 7/2008 | Dunki-Jacobs et al. |
| 2008/0188714 A1 | 8/2008 | McCaffrey |
| 2009/0018566 A1 | 1/2009 | Escudero et al. |
| 2009/0024158 A1 | 1/2009 | Viker |
| 2009/0062871 A1 | 3/2009 | Chin et al. |
| 2009/0105543 A1 | 4/2009 | Miller et al. |
| 2009/0156898 A1 | 6/2009 | Ichimura |
| 2009/0187080 A1 | 7/2009 | Seex |
| 2009/0240111 A1 | 9/2009 | Kessler et al. |
| 2009/0287061 A1 | 11/2009 | Feigenbaum et al. |
| 2009/0318765 A1 | 12/2009 | Torii |
| 2010/0004651 A1 | 1/2010 | Biyani |
| 2010/0022841 A1 | 1/2010 | Takahashi et al. |
| 2010/0076476 A1 | 3/2010 | To et al. |
| 2010/0114147 A1 | 5/2010 | Biyani |
| 2010/0151161 A1 | 6/2010 | Da Rolo |
| 2010/0161060 A1 | 6/2010 | Schaller et al. |
| 2010/0256446 A1 | 10/2010 | Raju |
| 2010/0280325 A1 | 11/2010 | Ibrahim et al. |
| 2010/0284580 A1 | 11/2010 | OuYang et al. |
| 2010/0286477 A1 | 11/2010 | OuYang et al. |
| 2010/0312053 A1 | 12/2010 | Larsen |
| 2011/0028791 A1 | 2/2011 | Marino et al. |
| 2011/0054507 A1 | 3/2011 | Batten et al. |
| 2011/0106261 A1 | 5/2011 | Chin et al. |
| 2011/0125158 A1 | 5/2011 | Diwan et al. |
| 2011/0130634 A1 | 6/2011 | Solitario, Jr. et al. |
| 2011/0295070 A1 | 12/2011 | Yasunaga |
| 2011/0319941 A1 | 12/2011 | Bar et al. |
| 2012/0095296 A1 | 4/2012 | Trieu et al. |
| 2012/0101338 A1 | 4/2012 | Cormac |
| 2012/0209273 A1 | 8/2012 | Zaretzka et al. |
| 2012/0221007 A1 | 8/2012 | Batten et al. |
| 2012/0232350 A1 | 9/2012 | Seex |
| 2012/0232552 A1 | 9/2012 | Morgenstern Lopez et al. |
| 2012/0298820 A1 | 11/2012 | Manolidis |
| 2012/0316400 A1 | 12/2012 | Vijayanagar |
| 2013/0103067 A1 | 4/2013 | Fabro et al. |
| 2013/0103103 A1 | 4/2013 | Mire et al. |
| 2013/0150670 A1 | 6/2013 | Cormac |
| 2013/0150674 A1 | 6/2013 | Haig et al. |
| 2013/0172676 A1 | 7/2013 | Levy et al. |
| 2013/0282022 A1 | 10/2013 | Yousef |
| 2013/0289399 A1 | 10/2013 | Choi et al. |
| 2013/0303846 A1 | 11/2013 | Cybulski et al. |
| 2013/0321395 A1* | 12/2013 | Chen ..................... G06T 17/05 |
| | | 345/419 |
| 2014/0066940 A1 | 3/2014 | Fang et al. |
| 2014/0074170 A1 | 3/2014 | Mertens et al. |
| 2014/0142584 A1 | 5/2014 | Sweeney |
| 2014/0148647 A1 | 5/2014 | Okazaki |
| 2014/0180321 A1 | 6/2014 | Dias et al. |
| 2014/0194697 A1 | 7/2014 | Seex |
| 2014/0215736 A1 | 8/2014 | Gomez et al. |
| 2014/0257489 A1 | 9/2014 | Warren et al. |
| 2014/0275799 A1 | 9/2014 | Schuele |
| 2014/0276840 A1 | 9/2014 | Richter et al. |
| 2014/0277204 A1 | 9/2014 | Sandhu |
| 2014/0318582 A1 | 10/2014 | Mowlai-Ashtiani |
| 2014/0357945 A1 | 12/2014 | Duckworth |
| 2015/0018622 A1 | 1/2015 | Tesar et al. |
| 2015/0018623 A1 | 1/2015 | Friedrich et al. |
| 2015/0065795 A1 | 3/2015 | Titus |
| 2015/0073218 A1 | 3/2015 | Ito |
| 2015/0112398 A1 | 4/2015 | Morgenstern Lopez et al. |
| 2015/0164496 A1 | 6/2015 | Karpowicz et al. |
| 2015/0216593 A1 | 8/2015 | Biyani |
| 2015/0223676 A1 | 8/2015 | Bayer et al. |
| 2015/0230697 A1 | 8/2015 | Phee et al. |
| 2015/0342621 A1 | 12/2015 | Jackson, III |
| 2015/0374213 A1 | 12/2015 | Maurice, Jr. |
| 2016/0015467 A1 | 1/2016 | Vayser et al. |
| 2016/0030061 A1 | 2/2016 | Thommen et al. |
| 2016/0066965 A1 | 3/2016 | Chegini et al. |
| 2016/0067003 A1 | 3/2016 | Chegini et al. |
| 2016/0074029 A1 | 3/2016 | O'Connell et al. |
| 2016/0095505 A1 | 4/2016 | Johnson et al. |
| 2016/0106408 A1 | 4/2016 | Ponmudi et al. |
| 2016/0166135 A1 | 6/2016 | Fiset |
| 2016/0174814 A1 | 6/2016 | Igov |
| 2016/0213500 A1 | 7/2016 | Beger et al. |
| 2016/0228280 A1 | 8/2016 | Schuele et al. |
| 2016/0235284 A1 | 8/2016 | Yoshida et al. |
| 2016/0287264 A1 | 10/2016 | Chegini et al. |
| 2016/0296220 A1 | 10/2016 | Mast et al. |
| 2016/0353978 A1 | 12/2016 | Miller et al. |
| 2017/0003493 A1 | 1/2017 | Zhao |
| 2017/0007226 A1 | 1/2017 | Fehling |
| 2017/0027606 A1 | 2/2017 | Cappelleri et al. |
| 2017/0042408 A1 | 2/2017 | Washburn et al. |
| 2017/0042411 A1 | 2/2017 | Kang et al. |
| 2017/0065269 A1 | 3/2017 | Thommen et al. |
| 2017/0065287 A1 | 3/2017 | Silva et al. |
| 2017/0086939 A1 | 3/2017 | Vayser et al. |
| 2017/0135699 A1 | 5/2017 | Wolf |
| 2017/0156755 A1 | 6/2017 | Poll et al. |
| 2017/0156814 A1 | 6/2017 | Thommen et al. |
| 2017/0189126 A1* | 7/2017 | Weir ..................... A61B 34/25 |
| 2017/0189127 A1 | 7/2017 | Weir |
| 2017/0196549 A1 | 7/2017 | Piskun et al. |
| 2017/0224391 A1 | 8/2017 | Biester et al. |
| 2018/0008138 A1 | 1/2018 | Thommen et al. |
| 2018/0098788 A1 | 4/2018 | White et al. |
| 2018/0214016 A1 | 8/2018 | Thommen et al. |
| 2018/0368656 A1 | 12/2018 | Austin et al. |
| 2019/0060029 A1* | 2/2019 | Kralicky ............. B25J 15/0019 |
| 2019/0149746 A1 | 5/2019 | Hyttinen et al. |
| 2019/0209154 A1 | 7/2019 | Richter et al. |
| 2019/0216454 A1 | 7/2019 | Thommen et al. |
| 2019/0254754 A1* | 8/2019 | Johnson ................ G06T 19/006 |
| 2022/0287793 A1 | 9/2022 | Lomeli et al. |

(56) References Cited

U.S. PATENT DOCUMENTS

FOREIGN PATENT DOCUMENTS

| | | | |
|---|---|---|---|
| DE | 29916026 U1 | 11/1999 | |
| EP | 0537116 A1 | 4/1993 | |
| EP | 0807415 B1 | 12/2003 | |
| EP | 4000499 A1 | 5/2022 | |
| GB | 2481727 B | 5/2012 | |
| WO | 1996029014 A1 | 9/1996 | |
| WO | 2001056490 A1 | 8/2001 | |
| WO | 2001089371 A1 | 11/2001 | |
| WO | 2002002016 A1 | 1/2002 | |
| WO | 2004103430 A2 | 12/2004 | |
| WO | 2008121162 A1 | 10/2008 | |
| WO | 2009033207 A1 | 3/2009 | |
| WO | 2013033426 A2 | 3/2013 | |
| WO | 2013059640 A1 | 4/2013 | |
| WO | 2014050236 A1 | 4/2014 | |
| WO | 2014100761 A2 | 6/2014 | |
| WO | 2014185334 A1 | 11/2014 | |
| WO | 2016111373 A1 | 7/2016 | |
| WO | 2016131077 A1 | 8/2016 | |
| WO | 2016168673 A1 | 10/2016 | |
| WO | 2017006684 A1 | 1/2017 | |
| WO | 2017015480 A1 | 1/2017 | |
| WO | 2017083648 A1 | 5/2017 | |

OTHER PUBLICATIONS

International Search Report and Written Opinion for Application No. PCT/US2015/048485, mailed Feb. 9, 2016. (16 pages).
International Search Report and Written Opinion for Application No. PCT/US2015/060978, mailed Feb. 15, 2016 (8 pages).
Invitation to Pay Additional Fees for Application No. PCT/US2016/050022, mailed Nov. 3, 2016 (2 pages).
International Search Report and Written Opinion for Application No. PCT/US2016/050022, issued Feb. 1, 2017 (19 pages).
International Search Report and Written Opinion for Application No. PCT/EP2022/056521, issued Jul. 13, 2022 (14 pages).
Iprenburg, M, "Percutaneous Transforaminal Endoscopic Discectomy: The Thessys Method," in Lewandrowski, K., et al., Minimally Invasive Spinal Fusion Techniques, Summit Communications, 2008 pp. 65-81.
Jung, K., et al., "A hands-free region-of-interest selection interface for solo surgery with a wide-angle endoscope: preclinical proof of concept," Surg Endosc, 2017, v. 31, pp. 974-980.

* cited by examiner

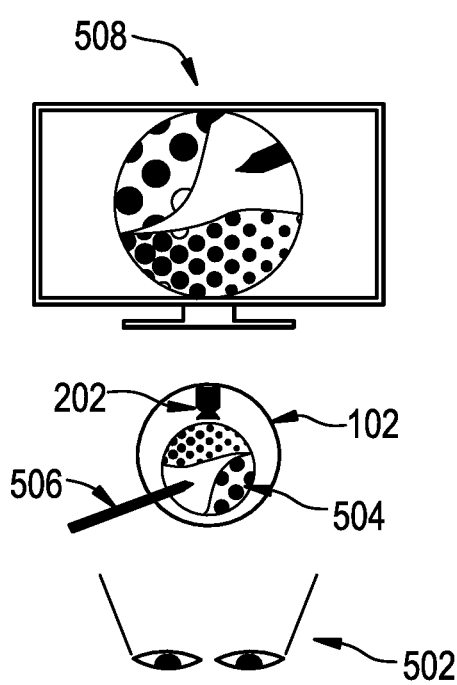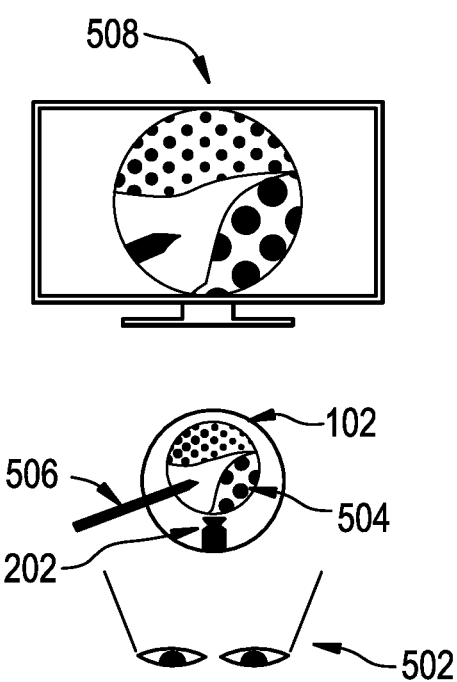

FIG. 7
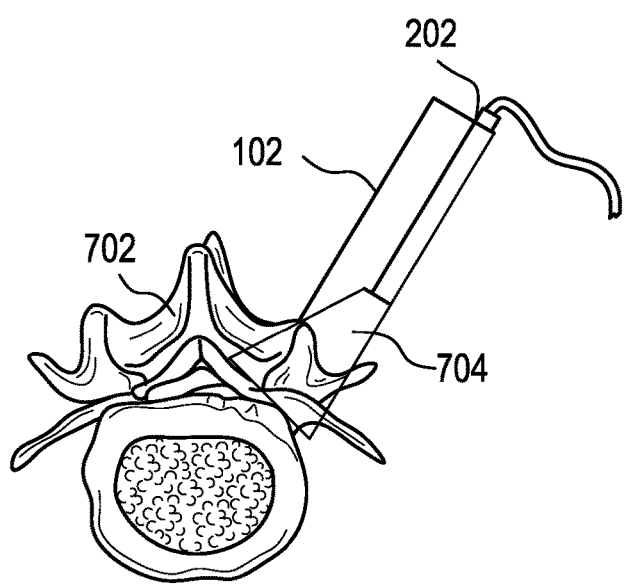
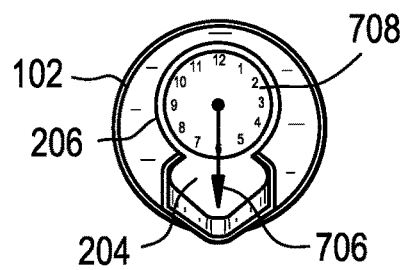
Camera in 6 o'clock
"Side-View" orientation
FIG. 8
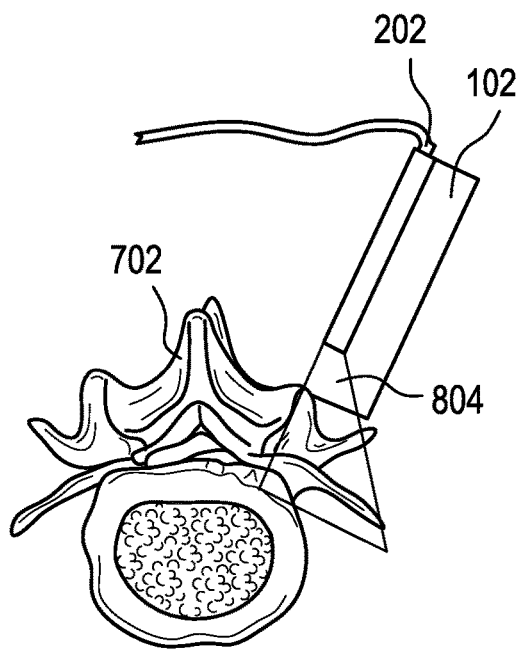
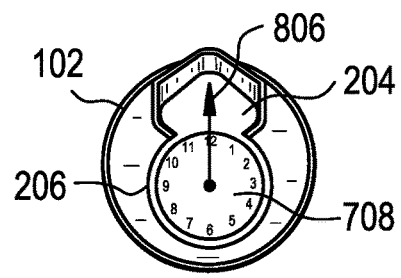
Camera in 12 o'clock
"Top-Down" orientation

FIG. 9A
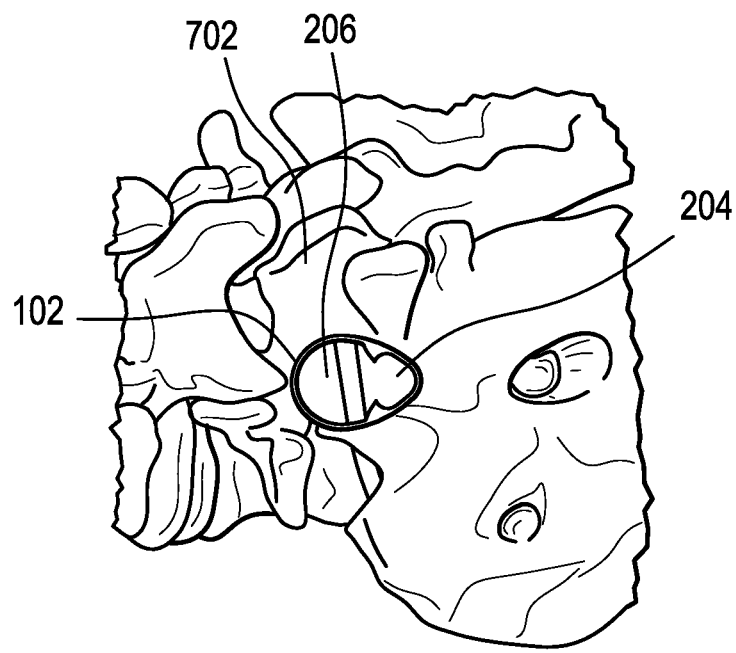
Camera in 3 o'clock
Interlaminar orientation
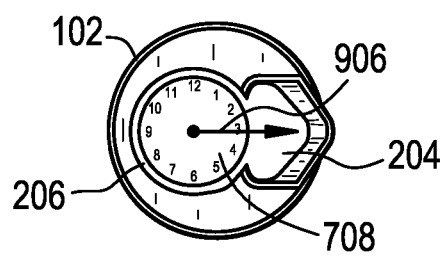

CAMERA POSITION INDICATION SYSTEMS AND METHODS

CROSS REFERENCE TO RELATED APPLICATIONS

This application is a continuation of U.S. patent application Ser. No. 17/200,750, filed Mar. 12, 2021. The entire contents of this application is incorporated herein by reference.

FIELD

Camera position indication systems and methods are disclosed herein, e.g., for conveying a camera's position to a user and/or adjusting a camera view display to match a user's perspective during a surgical procedure.

BACKGROUND

Many surgical procedures involve accessing a surgical site through a channel of an access device. For example, minimally-invasive surgical procedures often utilize one or more small incisions and access devices that extend through the incisions to provide a working channel from outside of a patient's body to a surgical site within the patient's body. In addition to passing surgical instruments, implants, and other components through such access devices, imaging devices such as cameras are also passed to provide a user with a view of the surgical site.

In cases where a camera or other imaging device is connected to an access device, e.g., when embedded in a channel that runs axially along a tube or other access device, or otherwise disposed in an access device or fixed relative to the access device so that it cannot rotate about its longitudinal axis within the access device, the position of the camera relative to the longitudinal axis of the access device may not be known and/or the orientation of an image displayed on a screen from the camera may not be the same as what a surgeon or other user sees when looking down the access tube directly. The mismatch between the surgeon or other user's perspective and the view of the camera within the access device can cause confusion, increase complexity of the surgical procedure, and possibly increase the likelihood of surgical error.

Accordingly, there is a need for improved systems and methods for conveying a camera's position to a user and/or adjusting a camera view display to match a user's perspective during a surgical procedure.

SUMMARY

Camera position indication systems and methods are disclosed herein for conveying a camera's position to a user and/or adjusting a camera view display to match a user's perspective during a surgical procedure. The systems and methods disclosed herein can ensure a user's perspective is properly reflected in a displayed camera view or provide feedback to a user that helps relate their perspective to the camera's position. The systems and methods provided herein also create a syntax or common language that helps users identify a difference between a user's perspective and a camera's position, and express a desired adjustment that can be used to align the two perspectives. This can be helpful in operating room environments where duties are divided among several people. For example, a surgeon can quickly identify a position of the camera from an indicator shown on a display with the camera output view. If the camera position and/or displayed output view does not match the surgeon or other user's perspective, the user can change the position of the access device and camera to better align with a desired perspective, and the indicator can be updated to show the new position by, e.g., the user calling out to an assistant or other user a desired camera position setting update. In other embodiments, the displayed output view can be adjusted using a transformation (e.g., rotation) of the output view on the display without moving the camera itself. This can be accomplished using the same syntax of camera position (e.g., to simulate a camera position move) or by directly naming a desired transition (e.g., rotate 180 degrees, etc.). The displayed output view from the camera can always include an indication of position to remind a viewing user of the camera's position and/or any transformation to the displayed camera output view. Control of the camera position indication and any desired transformations of the displayed view can be provided by, e.g., an assistant utilizing the syntax or common language to communicate with a surgeon or other user working directly on the patient. In other embodiments, a surgeon or other user can control these functions directly, e.g., using a remote control or other interface. In still other embodiments, an access device and/or camera can include one or more sensors to detect a position thereof and this information can be used to automatically control these functions.

In one aspect, a surgical method according to the present disclosure can include receiving an output view from a camera placed within a channel of an access device to view a surgical site within a patient, receiving an input of camera position from a user, and showing on a display the output view from the camera and an indication of camera position based on the input of camera position.

The systems, devices, and methods described herein can have a number of additional features and/or variations, all of which are within the scope of the present disclosure. In some embodiments, for example, the input can be received at a second display. This second display can be, for example, a display located remotely from a user working on a patient directly, such as a surgical technician assisting a surgeon and operating a controller or other equipment remote from the patient. In some embodiments, the second display can show the indication of camera perspective. The second display can also show the camera output view in some embodiments. The second display can be identical to the display or, in some embodiments, can be a smaller display, such as a display of a controller operating the system. In some embodiments, the second display can show the indication of camera perspective constantly and the display can show the indication of camera perspective temporarily in connection with orienting the output view of the camera on the display.

In some embodiments, any of the output view from the camera and/or the indication of camera position can be shown using an augmented reality display, e.g., a "heads up" display that places an output view and/or indication of camera position in a line of sight of a user as they directly view a patient, surgical site within a patient, etc. Such a display can be utilized in place of, or in addition to, a more conventional display, such as a liquid crystal display monitor, etc.

In certain embodiments, the input can be received using a control coupled to the camera. The control can be integrated into the camera, e.g., as part of a housing of the camera, wired inline between the camera and display, etc. In some embodiments, a remote control can be spaced apart from the camera and the display. The remote control can communicate the received input wirelessly in some embodiments, while in other embodiments the remote control can communicate the received input by wire. For example, in some embodiments the remote control can be wired in-line with the wire or cable that connects a system controller to the camera.

In some embodiments, the indication of camera perspective can be shown temporarily in connection with orienting the output view of the camera on the display. In other embodiments, the indication of camera perspective can be shown constantly. In certain embodiments, a small indicator of camera perspective can be shown constantly while a larger indicator of camera perspective can be shown temporarily in connection with orienting the output view of the camera on the display.

The indication of camera perspective can utilize any of a variety of forms to create an easy syntax for users to recognize and specify different camera orientations. In some embodiments, the indication of camera perspective can be any of a clock reading, a compass reading, a cardinal body direction, a circle degree reading, a quadrant, a spatial direction, a color, a reading from an alphabetic sequence, a reading from a numerical sequence, or a reading from a shape sequence.

In some embodiments, the method can further include receiving a second input of camera position from a user based on repositioning of the camera, and showing on the display the output view from the camera and an updated indication of camera position based on the second input of camera position.

In certain embodiments, the method can further include receiving from a desired transformation of the output view showed on the display based on a user perspective of the surgical site, and showing on the display a transformed output view from the camera based on the desired transformation and an updated indication of camera position reflecting the desired transformation.

In another aspect, a surgical system according to the present disclosure can include an access device configured to provide at least one channel to a surgical site within a patient, a camera configured to be disposed within the at least one channel of the access device to view the surgical site, a display, and a controller. The controller can be configured to receive an output view from the camera, receive an input of camera position from a user, and show on the display the output view from the camera and an indication of camera position based on the input of camera position.

As noted above, the systems, devices, and methods described herein can have a number of additional features and/or variations, all of which are within the scope of the present disclosure. In some embodiments, for example, any of the output view from the camera and/or the indication of camera position can be shown using an augmented reality display, e.g., a "heads up" display that places an output view and/or indication of camera position in a line of sight of a user as they directly view a patient, surgical site within a patient, etc. Such a display can be utilized in place of, or in addition to, a more conventional display, such as a liquid crystal display monitor, etc.

In certain embodiments, the system can further include a second display. The second display can, in some embodiments, be configured to receive the input. In certain embodiments, the controller can be further configured to show the indication of camera perspective on the second display. In some embodiments, the controller can be further configured to show the indication of camera perspective constantly on the second display and show the indication of camera perspective on the display temporarily in connection with orienting the output view from the camera on the display.

In certain embodiments, the system can further include a control coupled to the camera. The control can be integrated into the camera, e.g., as part of a housing of the camera, wired inline between the camera and display, etc. In some embodiments, a remote control can be spaced apart from the camera and the display. The remote control can communicate the received input wirelessly to the controller in some embodiments, while in other embodiments the remote control can communicate the received input by wire to the controller. In some embodiments, the controller can be further configured to show the indication of camera perspective temporarily in connection with orienting the output view of the camera on the display. In other embodiments, the controller can be further configured to show the indication of camera perspective constantly on the display.

In some embodiments, the controller can be further configured to show the indication of camera perspective as any of a clock reading, a compass reading, a cardinal body direction, a circle degree reading, a quadrant, a spatial direction, a color, a reading from an alphabetic sequence, a reading from a numerical sequence, or a reading from a shape sequence.

In certain embodiments, the controller can be further configured to receive a second input of camera position from a user based on repositioning of the camera, and show on the display the output view from the camera and an updated indication of camera position based on the second input of camera position.

In some embodiments, the controller can be further configured to receive a desired transformation of the output view showed on the display based on a user perspective of the surgical site, and show on the display a transformed output view from the camera based on the desired transformation and an updated indication of camera position reflecting the desired transformation.

Any of the features or variations described above can be applied to any particular aspect or embodiment of the present disclosure in a number of different combinations. The absence of explicit recitation of any particular combination is due solely to the avoidance of repetition in this summary.

BRIEF DESCRIPTION OF THE DRAWINGS

FIG. 5 is a schematic illustration of a first configuration where the perspective of a camera is not aligned with a user perspective;

FIG. 6 is a schematic illustration of a second configuration where the perspective of a camera is aligned with a user perspective;

FIG. 7 is a superior-view illustration of a configuration where a camera is disposed in a side view orientation;

FIG. 8 is a superior-view illustration of a configuration where a camera is disposed in a top view orientation;

FIG. 9A is a posterior-perspective-view illustration of an access device positioned relative to a surgical site;

DETAILED DESCRIPTION

Certain exemplary embodiments will now be described to provide an overall understanding of the principles of the structure, function, manufacture, and use of the devices, systems, and methods disclosed herein. One or more examples of these embodiments are illustrated in the accompanying drawings. The devices, systems, and methods specifically described herein and illustrated in the accompanying drawings are non-limiting example embodiments. The features illustrated or described in connection with one embodiment may be combined with the features of other embodiments. Such modifications and variations are intended to be included within the scope of the present disclosure. Additionally, like-numbered components of various embodiments can generally have similar features. Still further, sizes and shapes of assemblies, and/or components thereof, can depend at least on the anatomy of a subject with which the assemblies or components will be used, the size and shape of objects with which they will be used, and the methods and procedures in which they will be used.

Camera position or orientation indication systems and methods are disclosed herein for conveying a camera's position or orientation to a user and/or adjusting a camera view display to match a user's perspective during a surgical procedure. The systems and methods disclosed herein can ensure a user's perspective is properly reflected in a displayed camera view or provide feedback to a user that helps relate their perspective to the camera's position. The systems and methods provided herein also create a syntax or common language that helps users identify a difference between a user's perspective and a camera's position, as well as express a desired adjustment to align the two perspectives. This can be helpful in operating room environments where duties are divided among several people. For example, a surgeon can quickly identify an position of the camera and/or access device based on their manipulation of these components, e.g., as they position the access device and camera for use, and can easily call out to an assistant or other user a desired camera position setting. A displayed view from the camera can include an indication of position to remind a viewing user of the camera's position. Further, in some embodiments one or more desired transformations (e.g., rotations, inversions, etc.) can be performed on the displayed camera view in order to align the displayed view with the user's perspective. Control of the camera position indication and any desired transformations of the displayed view can be provided by, e.g., an assistant utilizing the syntax to communicate with a surgeon or other user working directly on the patient.

Figure 1:
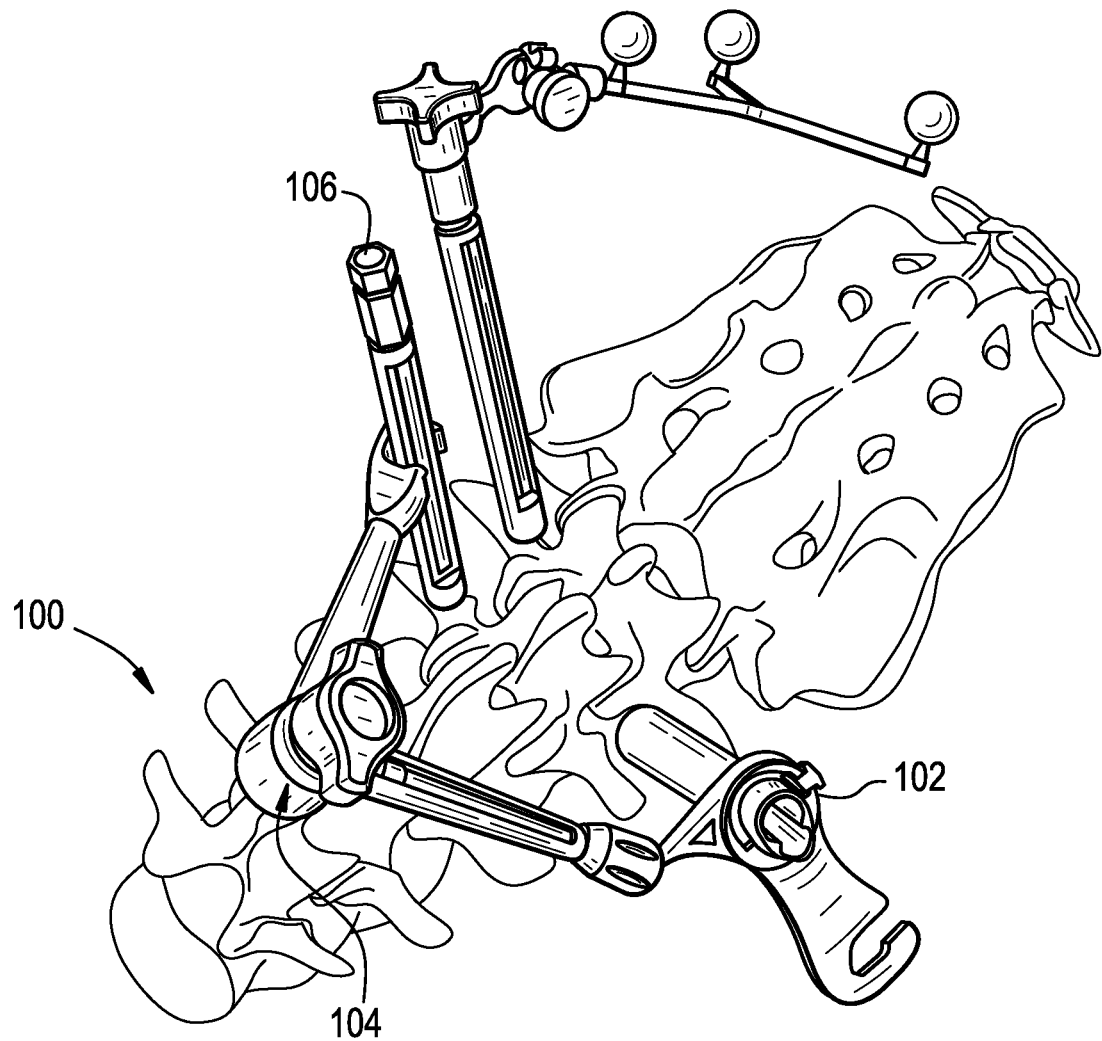
FIG. 1 is a perspective view of one embodiment of an access device providing at least one channel to a surgical site within a patient.

FIG. 1 illustrates one embodiment of a surgical system 100 in which the devices and methods described herein can be used, though it will be appreciated that such devices and methods can be used in various other applications instead or in addition. Further details on the system of FIG. 1 can be found in U.S. Publ. 2017/0156814, entitled "Multi-Shield Spinal Access System," U.S. Publ. No. 2019/0209154, entitled "Multi-Shield Spinal Access System," and US 2019/0216454, entitled "Surgical Instrument Connectors and Related Methods." The entire contents of each of these publications are incorporated by reference herein. The system 100 can be used in various surgical procedures, including spinal surgeries such as microsurgical bone resection, spinal decompression, spinal fusion, and the like. In general, the system 100 can include any one or more of an access device 102, a tissue retractor (not shown), a pedicle post or other anchor 106, a connector 104, and a camera (see FIG. 2). Example access devices 102 are disclosed in U.S. Pat. No. 10,758,220, entitled "Devices and Methods for Providing Surgical Access;" example tissue retractors are disclosed in U.S. Pat. No. 10,779,810, entitled "Devices and Methods for Surgical Retraction;" example connectors 104 are disclosed U.S. Publ. No. 2019/0216454 mentioned above; example anchors 106 are disclosed in U.S. Publ. No. 20180098788, entitled "Surgical Access Port Stabilization;" and example cameras are disclosed in U.S. Publ. No. 2018/0008138, entitled "Surgical Visualization Systems and Related Methods." The entire contents of each of these publications are incorporated by reference herein.

An exemplary method of using the system 100 of FIG. 1 can include any one or more of the following steps, performed in any of a variety of sequences: a) making an incision in a skin of a patient; b) percutaneously inserting through the incision an access device 102 having a substantially tubular shape (such as a tube or a multi-slotted retractor), the access device having a length adapted to extend from the incision to a border between sensitive and insensitive tissue (e.g., a superior articular process (SAP), or a lamina) in the spine of the patient; c) stabilizing the access device to an anchor 106 (e.g., a pedicle anchor) using a connector 104; d) inserting an access device integrated optical visualization instrument (see FIG. 2); e) resecting a portion of the superior articular process, and/or performing a microsurgical decompression procedure; f) inserting or deploying a tissue retractor through or from the access device so that a distal end portion of the tissue retractor extends to the intervertebral disc, the retractor having an outer surface; g) contacting the outer surface of the retractor to a nerve root to shield the nerve root; h) microsurgically decompressing any tissue deemed to be causing nerve impingement; i) extracting intervertebral disc material including removing cartilaginous material from the vertebral endplates; j) inserting an interbody device; and k) deploying a mechanism of stabilization to stabilize the intervertebral segment.

Figure 2:
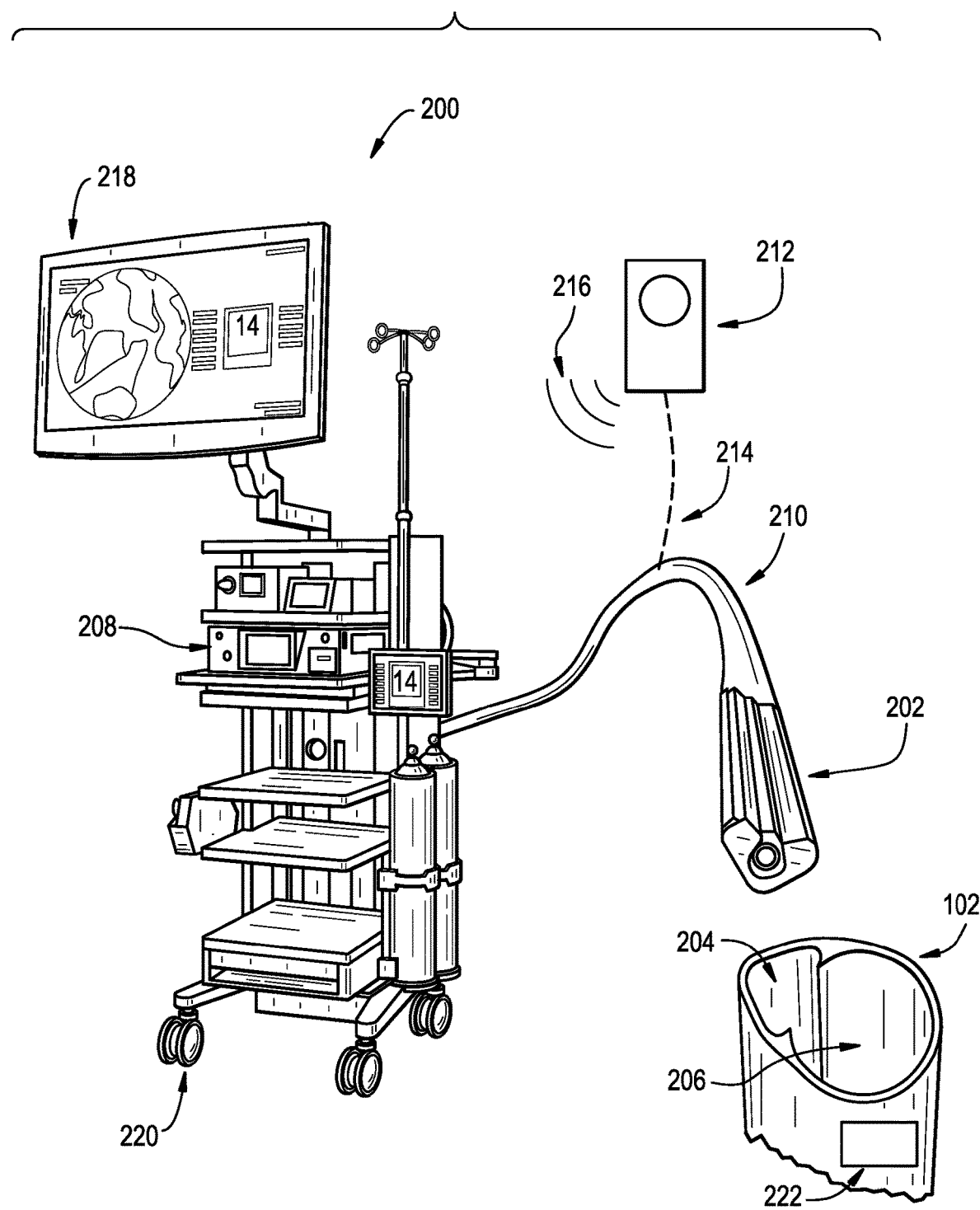
FIG. 2 is a perspective view of one embodiment of a system according to the present disclosure.

FIG. 2 illustrates one embodiment of a camera system 200 that can be used in connection with the surgical system 100 described above. The system 200 can include a camera or other visualization instrument 202 that can be configured to pass through the access device to reach and visualize a surgical site. For example, the camera 202 can be configured to pass through a visualization channel 204 of the access device 102 and be positioned within the channel at any of a variety of positions along the length of the access device. From such a position, the camera 202 can view a working channel 206 of the access device 102 and/or a surgical site distal to a distal end of the access device. The camera 202 can be coupled to the access device 102 using, e.g., an interference fit, such the camera can be positioned anywhere along the axis of the visualization channel 204 and provide multiple viewing options. Further, the access device 102 can be configured for rotation about its longitudinal axis, thereby enabling the camera to be moved to any position around the longitudinal axis of the access device.

The camera 202 can be coupled to a controller 208 via one or more cables 210 in some embodiments or, in other embodiments, can communicate with a controller or other processor via wireless communication. The controller 208 can include a digital data processor, one or more storage memories, one or more inputs and outputs, and other components of conventional electronic controllers or computing devices. The controller 208 can include one or more user interfaces for controlling the camera 202, as explained in more detail below, or can be coupled to one or more input devices, such as a control or remote control 212, that can be used to control the camera 202 and/or controller 208. The control 212 can be coupled to the camera 202 and/or controller 208 by a wired connection 214 or by wireless communication 216. In some embodiments, the control 212 can be integrated into the camera, e.g., as part of a housing of the camera, can be wired inline between the camera and the display, or can be an intermediate control disposed between the camera and the display, etc.

The controller 208 and/or camera 202 can also be coupled to one or more displays 218 that can be configured to present a variety of data to a user, including the view of a working channel and/or surgical site provided by the camera 202. The various components of the system 200 can be integrated into a mobile cart 220 as shown, or can be disposed separately about a surgical operating environment. Moreover, in some embodiments the components of the system 200 can be arranged for interaction with a plurality of users. For example, in some embodiments a surgeon or other user can be positioned near a patient and surgical site where they might directly manipulate the access device 102 and camera 202. The display 218 might be arranged to be viewable by the surgeon and the controller 208 can be positioned adjacent an assistant or other user that might be more remotely located from the patient within the surgical operating environment. In other embodiments, the remote control 212 can be positioned for use by the surgeon or any other user, e.g., as a foot control, hand control, etc. Still further, in some embodiments the system 200 can further include a sensor 222 coupled to, or integrated into, the access device 102 and configured to detect an orientation of the access device that can be utilized to determine a perspective of the camera 202, as explained in more detail below. In still other embodiments, such a sensor can be integrated into the camera 202 rather than the access device 102.

Still further, in some embodiments the display 218 can include an augmented reality display, e.g., a "heads up" display that places an output view from the camera 202 and/or other information, such as an indication of camera position as described below, in a line of sight of a user as they directly view a patient, surgical site within a patient, etc. Such a display can be utilized in place of, or in addition to, a more conventional display as illustrated in FIG. 2, such as a liquid crystal display monitor, etc.

Figure 3:
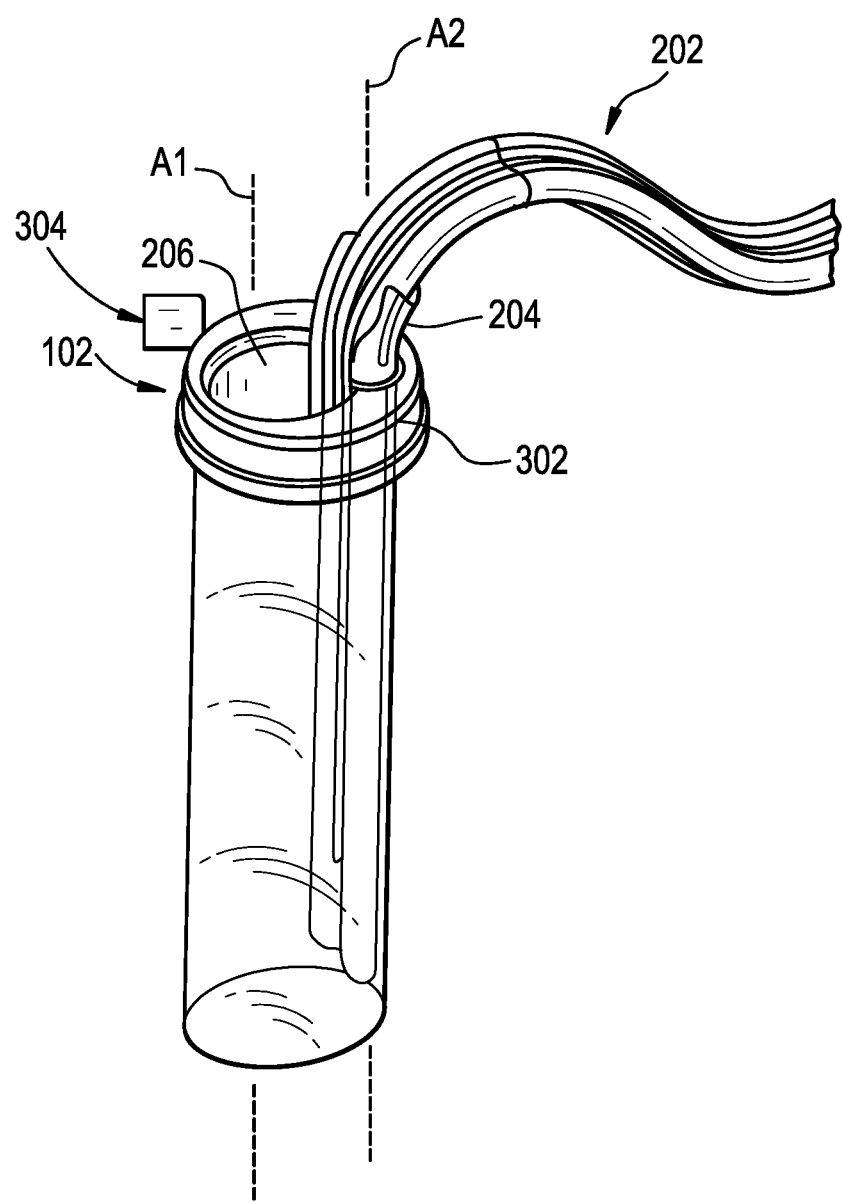
FIG. 3 is a perspective view of one embodiment of a camera disposed within a channel of an access device.

FIG. 3 illustrates further details of an access device 102 with a camera 202 disposed therein for viewing a working channel and/or surgical site adjacent a distal end of the access device. The access device 102 can include an elongate body having proximal and distal ends. The access device 102 can define a working channel 206 extending between the proximal and distal ends and having a central longitudinal axis A1. The working channel 206 can be cylindrical. The working channel 206 can have a circular transverse cross-section. The working channel 206 can have a diameter in the range of about 3 mm to about 30 mm, in the range of about 10 mm to about 20 mm, and/or in the range of about 12 mm to about 15 mm. The working channel 206 can have a diameter of about 15 mm in some embodiments. While a single working channel 206 is shown, the access device 102 can include any number of working channels. In use, instruments and/or implants can be disposed in, passed through, and/or inserted into the working channel 206 to perform a surgical procedure. In some embodiments, the access device 102 can be used to access an intervertebral disc space. A cutting instrument can be inserted through the working channel 206 to cut tissue, such as bone or disc tissue. An aspiration instrument can be inserted through the working channel 206 to aspirate material from the disc space, including excised bone or disc tissue. The cutting instrument and the aspiration instrument can be a single tool in some embodiments. An implant such as a fusion cage, a height and/or width expandable fusion cage, a disc prosthesis, or the like can be inserted into the disc space through the working channel 206.

The access device 102 can define a visualization channel 204. The visualization channel 204 can extend between the proximal and distal ends of the access device 102, or can extend along less than an entire length of the access device. The visualization channel 204 can include a central longitudinal axis A2. The central axis A2 of the visualization channel 204 can be disposed radially-outward from the central axis A1 of the working channel 206. The working channel 206 can have a greater transverse cross-sectional area than the visualization channel 204. The visualization channel 204 can be open to, or can intersect with, the working channel 206 along its length. The visualization channel 204 can be isolated or separate from the working channel 206 in some embodiments.

The visualization channel 204 can have an interior transverse cross section that matches or substantially matches the exterior transverse cross-section of the camera 202. When disposed within the visualization channel 204, an exterior surface of the camera 202 can define at least a portion of the inner sidewall of the working channel 206. The working channel 206 can be cylindrical about the central axis A1 and the surface of the camera 202 that faces the working channel can form a section of a cylinder centered on the axis A1. The inner sidewall of the working channel 206 and the outer surface of the camera 202 can define a substantially smooth and continuous surface.

The access device 102 can include an attachment feature 302, e.g., for attaching the access device to a support or other object and enabling rotation of the access port about its longitudinal axis. The attachment feature 302 can be formed at a proximal end of the access device 102. For example, the access device 102 can include an annular circumferential groove 302 formed in an exterior surface thereof. A variety of other attachment features 302 are also possible, e.g., a ball and/or socket feature for connecting with a complementary feature on a connector or other component, etc.

The access device 102 can have an exterior transverse cross section that is circular, can have an exterior transverse cross section that is oblong or egg-shaped, or can include any of a variety of other exterior transverse cross sectional shapes. The access device 102 can have an external diameter or dimension in the range of about 5 mm to about 30 mm, in the range of about mm to about 25 mm, and/or in the range of about 15 mm to about 22 mm. The access device 110 can have an external diameter or dimension of about 17 mm. The exterior surface of the access device 102 can be roughened, ribbed, milled, or coated with or formed from a material having a high coefficient of friction, which can advantageously improve grip and stability with surrounding tissue when the access device is inserted into a patient.

Figure 4:
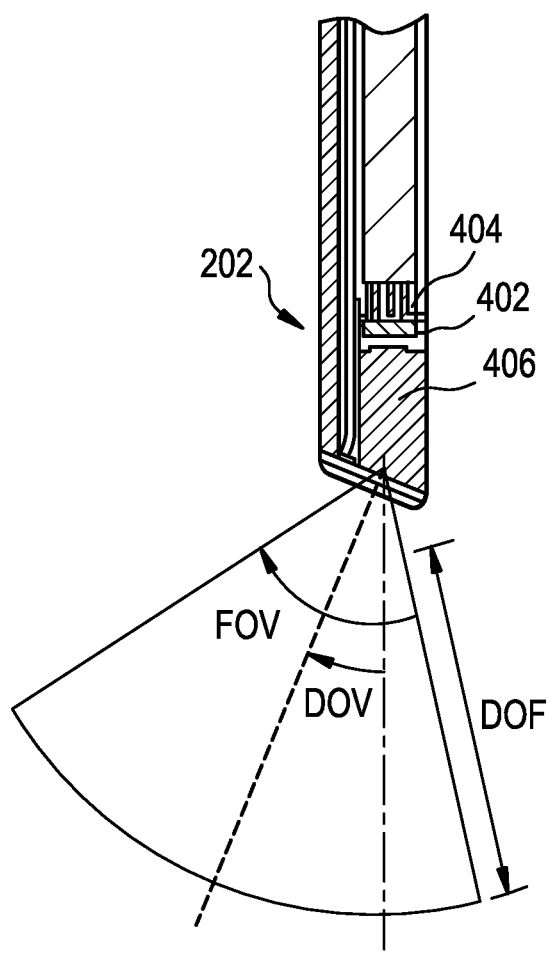
FIG. 4 is a cross-sectional side view of the camera of FIG. 3.

FIG. 4 illustrates a side cross-sectional view of the camera 202. The camera 202 can include an image capture sensor 402, such as a charge-coupled device (CCD) or complementary metal-oxide-semiconductor (CMOS) sensor, as well as an associated lighting device 404, such as a fiber optic that delivers light from an external source or one or more light emitting diodes (LEDs) or other light generating devices that can be integrated into the camera 202. The camera 202 can also include a lens assembly 406 that can include one or more lenses to help focus the view of the sensor 402 in a desired manner. The camera 202 can have a field-of-view (FOV), a direction of view (DOV), and a depth of field (DOF). In some embodiments, the FOV can be in the range of about 60 to about 70 degrees. In some embodiments, the DOV can be in the range of about 15 to 30 degrees. In some embodiments, the DOV can be in the range of about 20 to 25 degrees. In some embodiments, the DOV can be about 22.5 degrees. In some embodiments, the DOF can be in the range of about 7 mm to about 40 mm. Further details of example cameras can be found in US 2018/0214016, entitled "Surgical Visualization Systems and Related Methods," the entire contents of which are incorporated by reference herein.

FIG. 5 illustrates one embodiment of a difficulty that can occur with cameras disposed in access devices to view surgical sites within a patient's body. A user 502 is standing toward the bottom of the page in the view of the figure and their perspective is toward the top of the page in the view of the figure. As the user looks down the access device 102 directly, they see the view 504 and can, for example, manipulate an instrument 506 inserted through the access device. The camera 202, however, can be oriented differently from the user 502. For example, as shown in FIG. 5, the camera 202 can be disposed in a visualization channel of the access device that positions the camera opposite the user (i.e., toward the top of the page in the view of the figure). As a result, the camera's position, perspective, or orientation can be opposite that of the user 502, resulting in an image on the display 508 that would appear to be upside down to the user 502 viewing the display. This can cause confusion in the operating environment and increase complexity, time, and likelihood of error in completing a surgical procedure.

In contrast to the configuration of FIG. 5, the configuration of FIG. 6 shows the camera 202 disposed in the access device 102 in a manner that is aligned with a perspective of the user 502. As a result, the image of the surgical site from the camera 202 that is shown on the display 508 is aligned with the perspective of the user 502 and can facilitate a much more intuitive experience in performing a surgical procedure.

The mismatch between the camera position and the user position can create an unexpected output view display that can confuse the user, and systems and methods according to the present disclosure provide a syntax or common language for expressing the position of the camera as a location around a circle and an indicator on the display 508 to inform the user of the camera position. This can allow the user to identify and internally relate the displayed camera view perspective to their own perspective. Moreover, in some embodiments, the syntax and camera position indication can facilitate a user manually adjusting a position of the access device, e.g., by rotating it about its longitudinal axis between the configurations shown in FIGS. and 6, in order to align a perspective of a camera 202 with their own direct perspective. Still further, the systems and methods described herein can facilitate any of a variety of transformations of the displayed output view of the camera to better align with the user perspective. For example, in some embodiments a particular manipulation of the access device and/or camera might not always be possible or desirable, as described in more detail below. Accordingly, it can be desirable to provide a mechanism for switching a displayed perspective or orientation of an output view shown on a display to align it with a user's perspective rather than physically reorienting an access device and/or camera to match the user's perspective. In FIGS. for example, the output view of the camera 202 can be rotated 180 degrees without moving the camera as shown in FIG. 6 to achieve a similar effect.

The present disclosure therefore provides systems, devices, and methods for achieving perspective matching by providing a user with a representative syntax or common language to express a camera's position or orientation and a displayed indication of camera position or orientation that can be used to easily express a current and/or desired position, orientation, or perspective of the camera and/or displayed output view of the camera shown on a display. This can allow a user to easily adjust a position of the camera or an orientation of a displayed output view of the camera to match their own direct perspective and/or allow a user to easily communicate with one or more other users among a surgical team to efficiently achieve such perspective matching in embodiments where a different user controls operation of the camera and placement of the camera and/or access port.

FIGS. 7 and 8 illustrate another example of how differences in perspective can develop during use of cameras introduced to a surgical site through an access device, as well as how physical reorientation or repositioning of the camera may not always be ideal. Also pictured is one embodiment of a representative syntax or common language that can be employed to describe the position of the camera as a location about a circle and instruct any desired change to the camera position and/or displayed output view.

FIG. 7 illustrates a configuration wherein an access port 102 is positioned laterally or posterolaterally relative to a patient's vertebra 702 and oriented such that a visualization channel and camera 202 disposed therein are in an anterior and lateral position of the access port. Such positioning can be desirable in certain instances to provide a field of view 704 that is as laterally-oriented as possible, i.e., a "side view" orientation or configuration. As shown in the lower part of the figure, such positioning can be expressed using the syntax of a clock face 708, e.g., that the camera is in a 6 o'clock position 706 when viewed from above.

If this camera position is misaligned with a perspective of a user standing near the patient and viewing an output display of the camera, it can be helpful to provide the user with an indication of the camera position using the clock face 708 syntax. This can allow the user to better visualize the camera's position and relate any displayed output view of the camera to their direct view of the patient and surgical site.

Further, in some embodiments a user may wish to change the camera position or orientation, either to better align the displayed camera output view with their own perspective or to better or differently view patient anatomy. In such a case, a user can directly manipulate the access device 102 and/or camera 202, e.g., by rotating the access tube 180 degrees into the configuration of FIG. 8, for example, where the camera 202 is disposed in a posterior and medial position of the access port. Following such a move, a user may want to indicate to others in the surgical environment the new position of the camera 202 and/or have any displayed camera position indication updated to match the new camera position. This can be done using the representative syntax or common language of the clock face 708. For example, a user can declare the new camera to be in the 12 o'clock position 806, and an assistant or other user operating a controller 208 can enter the update to the displayed camera position indicator. Alternatively, the user manipulating the access device 102 and/or camera 202 can themselves provide an input to the controller 208 to update the camera position indicator. For example, the user can directly interface with the controller 208, or can utilize a wired or wireless remote control 212 to enter the new camera position. Still further, in some embodiments, one or more sensors incorporated into the access device 102 and/or camera 202 can detect the change in position and automatically adjust the displayed camera position indicator, as described in more detail below.

In some embodiments, however, moving the access device 102 or camera 202 may not be desirable. For example, such a move might change the field of the view of the camera 202 in an undesirable manner. In the embodiment of FIGS. 7 and 8, for example, a change in camera position from that shown in FIG. 7 to that shown in FIG. 8 might change the field of view 704 into the field of view 804 that is a more posterior, "top down" orientation that might not be as desirable as the more lateral field of view 704. Of course, in some embodiments the situation might be reversed, such that the posterior, "top down" view of FIG. 8 is desirable and physically reorienting the camera 202 away from this positioning is undesirable.

In such embodiments, it can be desirable to perform one or more transformations to the displayed output view of the camera without physically moving the camera. For example, the output view of the camera can be rotated 180 degrees on the display 218 (e.g., by a function of the controller 208) to maintain the field of view 704 but provide a perspective that can be better aligned to a user who might prefer the camera positioning of FIG. 8. Such transformations (e.g., rotations, inversions, etc.) can be specified by a user with the same representative syntax or common language as the camera position indication. For example, a user can express that the camera is positioned in the 6 o'clock position but that they would prefer the display to simulate the 12 o'clock position. Alternatively, the transformations can be expressed as direct changes to the displayed output view, e.g., rotation of 180 (or other number of) degrees, horizontal flip, vertical flip, etc. Any transformations can be reflected using the displayed camera position indicator in the same manner as an actual camera position change, or can be expressed in a separate indicator or some other differentiated manner from a true position change of the camera.

Figure 9B:
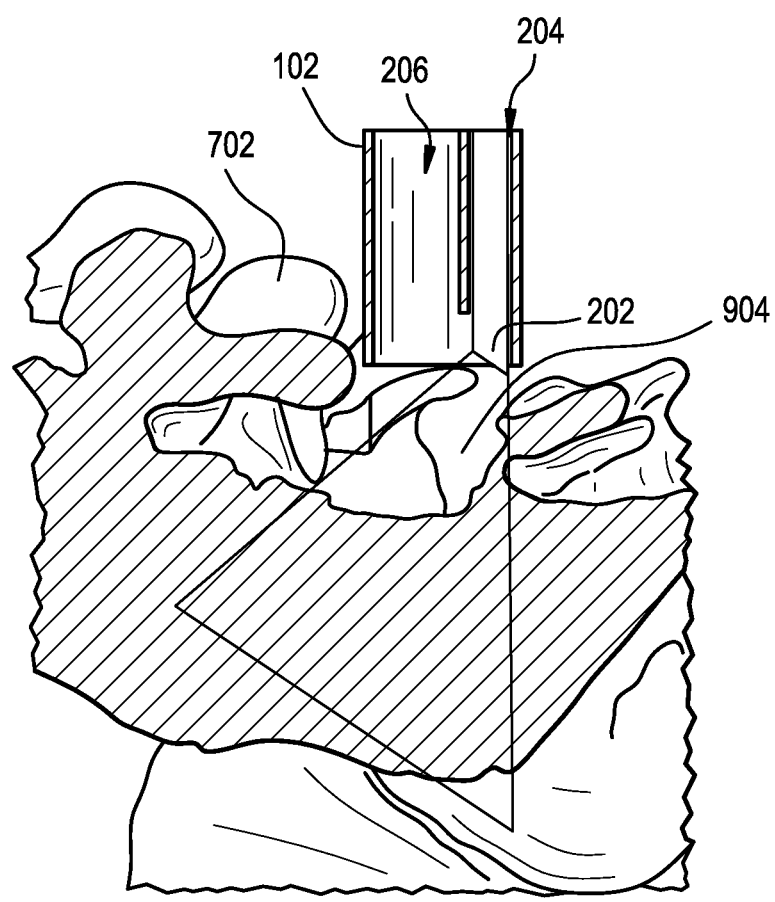
FIG. 9B is a lateral-perspective-view illustration of the access device of FIG. 9A with a camera disposed therein.

FIGS. 9A and 9B illustrate a further possible position of a camera and the syntax representation of that perspective that can be employed to indicate the position of the camera. FIG. 9A illustrates a posterior view of an access device 102 that is positioned in an interlaminar orientation to access, e.g., an intervertebral disc during a spinal fusion procedure. Consistent with the clock-face 708 syntax described above in connection with FIGS. 7 and 8, it can be said that the visualization channel 204 of the access device 102 and any camera 202 disposed therein (see FIG. 9B, not shown in FIG. 9A) is at a 3-o'clock position 906. Such positioning of the access device 102 and camera 202 can be desirable, e.g., for the particular field of view 904 provided to the camera 202 in this position, as shown in the lateral view of FIG. 9B.

As noted above, however, the displayed output view of the camera 202 may not align with a user perspective if the position of the camera 202 and the user are not the same or at least aligned relative with one another. The mismatch between the displayed output view and the user perspective can cause confusion or slow progress during a procedure. One way to address this is to provide a camera position indication in connection with the displayed output view of the camera, which can facilitate a user recognizing the camera position and any possible mismatch between their perspective and the displayed output view perspective. The camera position indication can be, for example, the position of the camera about a clock face 708, as described in connection with FIGS. 7-9, or any of a variety of other syntaxes or languages that describe a position about a circle (see further examples below).

Use of such a camera position or orientation indication can also allow a user to quickly reposition the access device 102 and/or camera 202 and input to the controller 208 an update to the camera position using similar syntax. This update can be entered by the user directly at the controller 208, using a remote control 212, or by communicating to a second user, such as an assistant, etc., a desired new position that they can enter. In still other embodiments, one or more sensors integrated into the access device 102 and/or camera 202 can detect any change in position and automatically update the displayed camera position indication.

Still further, in some embodiments it can be desirable to enable one or more transformations (e.g., rotation, inversion, etc.) of the displayed output view of the camera to provide a more intuitive experience for the user without repositioning the camera. Any desired transformation can be communicated using similar syntax (e.g., rotation of degrees according to a new desired clock face position, etc.), by direct call-out or entry into a user interface (e.g., 180 degree rotation, etc.), etc. Further, any transformation implemented without movement of the camera can be reflected in the camera position indication by, e.g., updating the indication to simulate a move of the camera, including a separate indication of transformation in addition to an indication of true camera position, etc.

Figure 10:
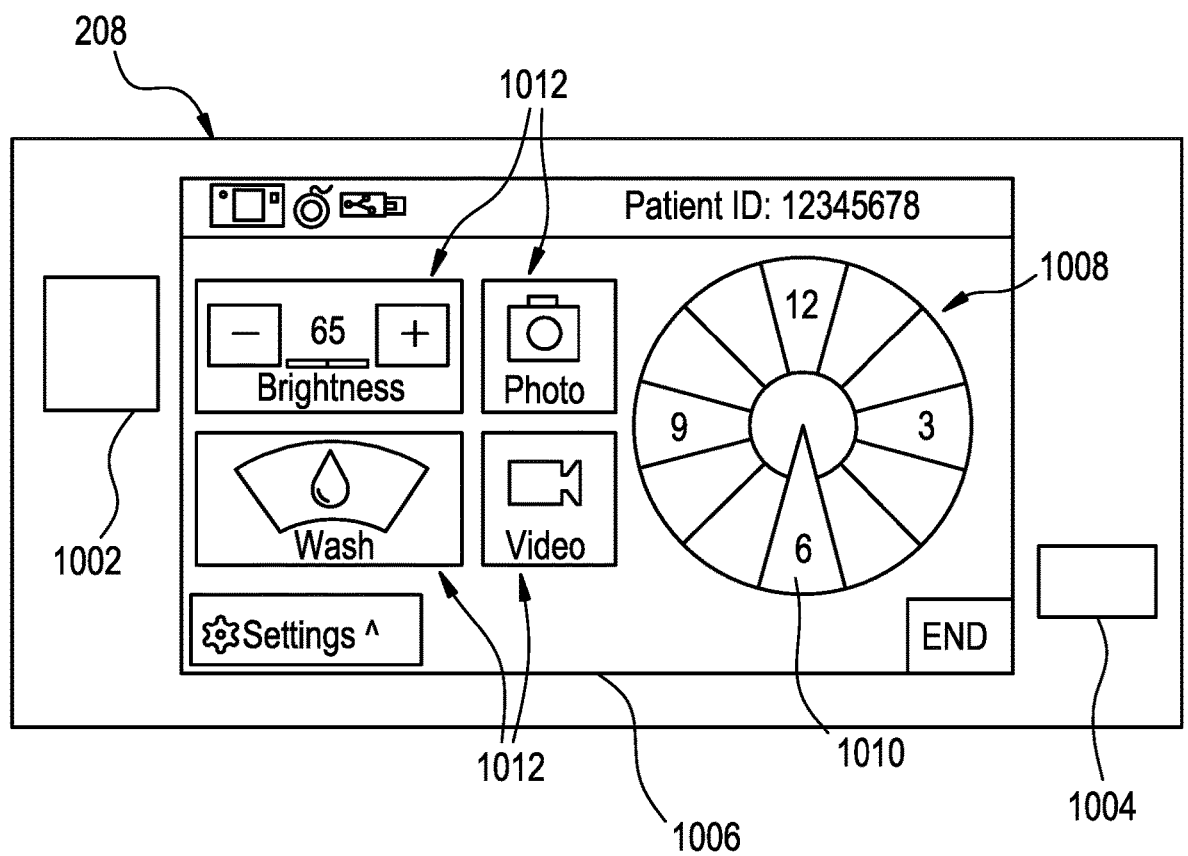
FIG. 10 is a front-view illustration of a controller and display with an indication of camera perspective according to the present disclosure.
Figure 11:
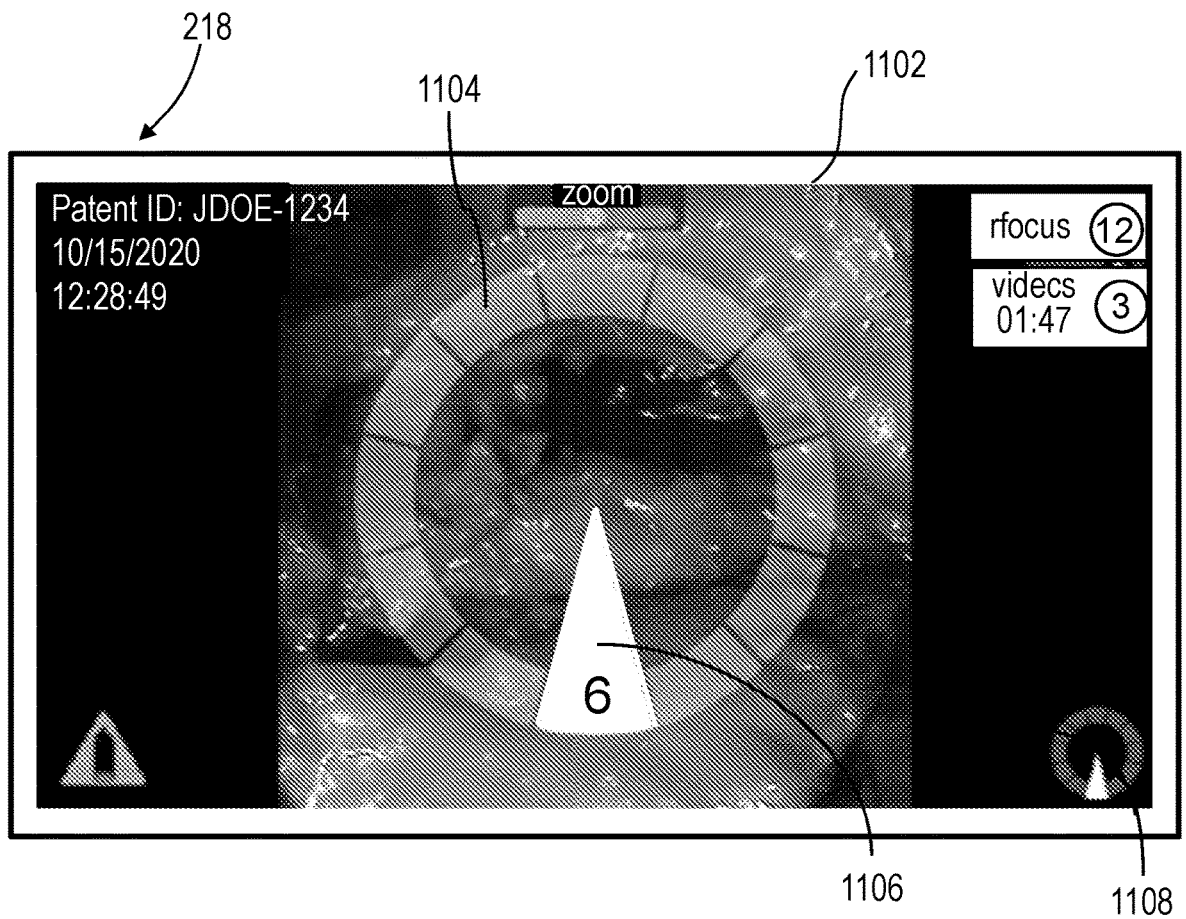
FIG. 11 is an illustration of a display including an indication of camera perspective according to the present disclosure.

FIGS. 10 and 11 illustrate one embodiment of a camera controller 208 and display 218 that can be included in the above-described system 200. FIG. 10 illustrates a front-view of the camera controller 208. The controller 208 can include one or more physical inputs 1002 and/or outputs 1004, such as buttons, knobs, switches, etc., as well as ports (e.g., Universal Serial Bus or USB ports, Secure Digital or SD card ports, etc.). The controller 208 can also include a display 1006 that can be touch sensitive to enable control or receipt of user input through the display. In other embodiments, as described above, the controller can be coupled to a remote input device, such as remote control 212, or can receive inputs from another computer or controller coupled to the controller 208 by a network via wired or wireless communication protocols.

The display 1006 of the controller 208 can include a graphical representation 1008 of the camera position or orientation, e.g., as a position about a circle expressed as a reading on a clock face, etc. As shown in FIG. 10, for example, the current camera position 1010 can be highlighted and/or emphasized in some manner, e.g., by making the selection a different color, larger font, bolder font, etc. Further, a user can enter a new or updated camera position by pressing the display 1006 or using an input 1002 (e.g., a knob, etc.) to select the new position in connection with movement of the camera by a user. In addition, a number of other functions of the camera 202, e.g., illumination brightness, lens washing, photo or video capture, output view transformations, etc., can be controlled using the display 1006 via graphical user interface buttons 1012.

FIG. 11 illustrates the display 218 that corresponds to the controller display 1006 shown in FIG. 10. The display 218 can show the output view 1102 of the camera 202, as well as one or more indicators of camera position. For example, the display 218 can include a persistent indicator 1108 of camera position that remains present on the screen at all times. The indicator 1108 can be small in size relative to the displayed view 1102. In addition, the display 218 can include a temporary indicator 1104 that can be displayed, for example, whenever a change in camera position is specified, e.g., using the input interface of the display 1006 on the controller 208. The temporary indicator 1104 can be larger and more prominent than the persistent indicator 1108, e.g., it can be centered on the display and take up a large portion of the displayed view 1102. The indicators 1104, 1108 can match the indicator 1008 on the controller 208.

Figure 12:
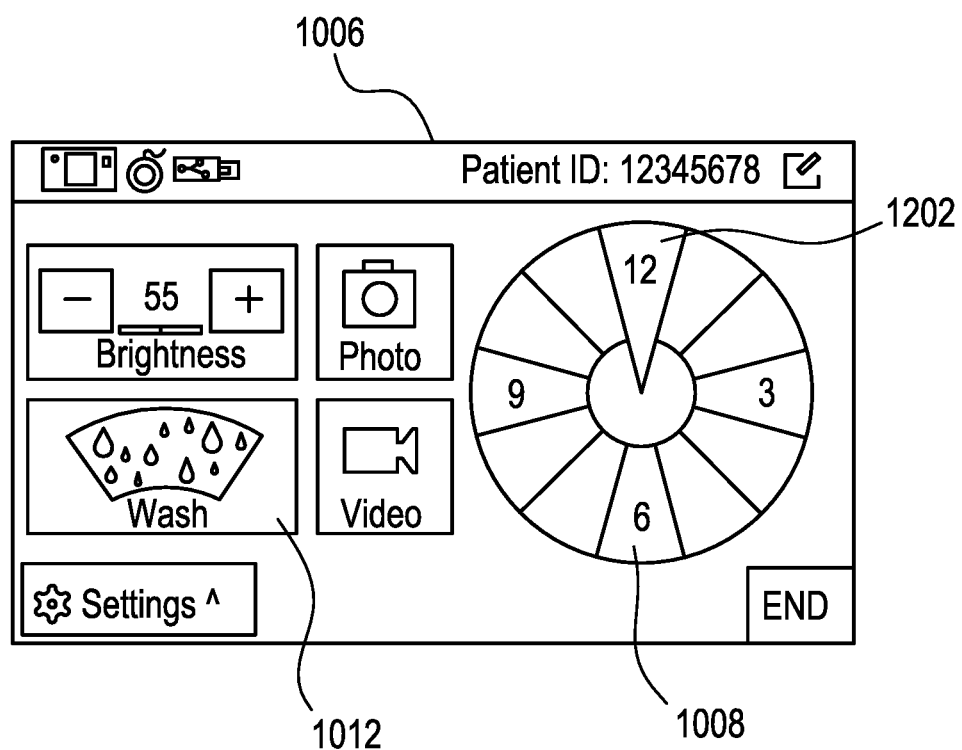
FIG. 12 is an illustration of a controller user interface according to the present disclosure.
Figure 13:
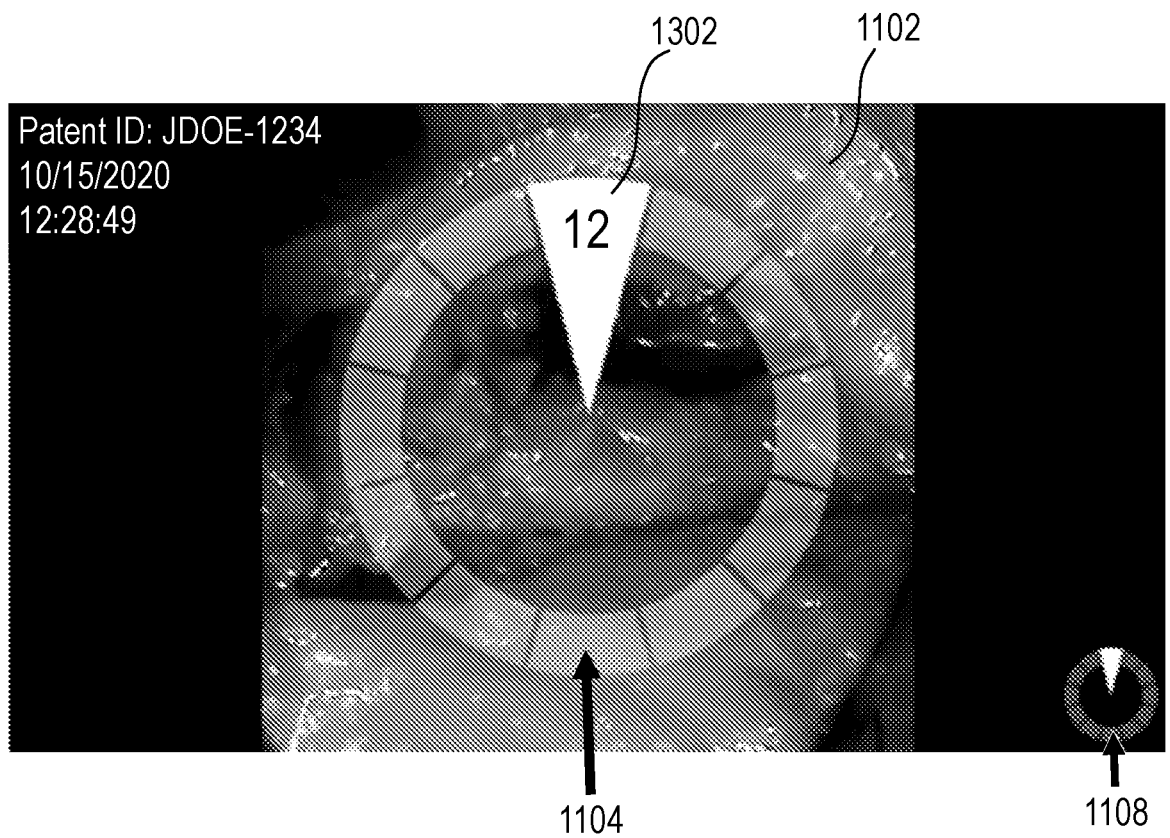
FIG. 13 is an illustration of a display including an indication of camera perspective according to the present disclosure.

FIGS. 12 and 13 illustrate the graphical displays of the controller 208 and display 218 in a different configuration where the camera position has been changed from that displayed in FIGS. 10 and 11. For example, while the displays of FIGS. 10 and 11 show the camera in the 6-o'clock position 1010, 1106 in the syntax of a clock face, e.g., as shown in FIGS. 6 and 7, the displays of FIGS. 12 and 13 show the camera position changed to a 12-o'clock position 1202, 1302, e.g., as shown in FIGS. 5 and 8.

Figure 14:
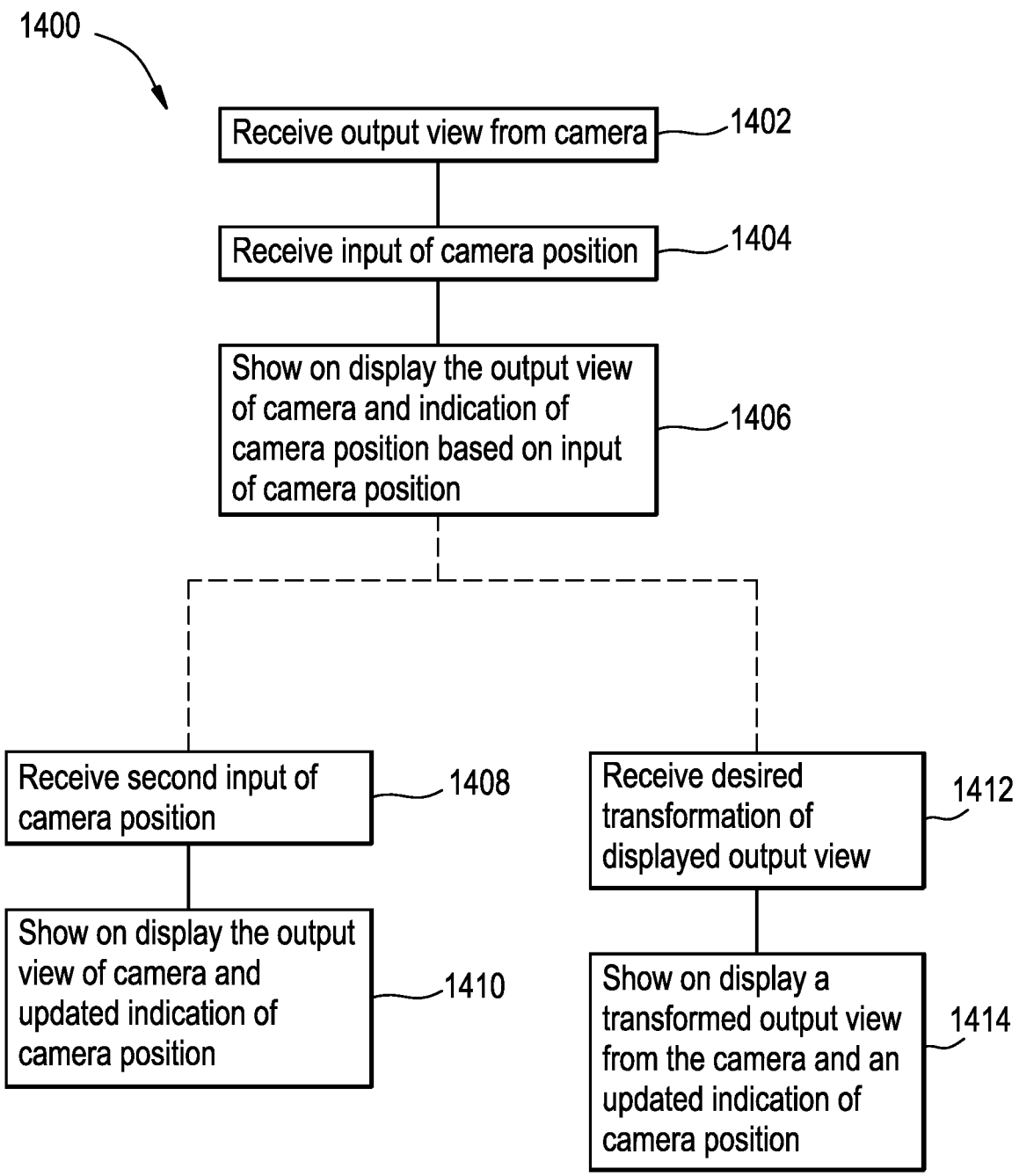
FIG. 14 an illustration of one embodiment of a method according to the present disclosure.
Figure 15:
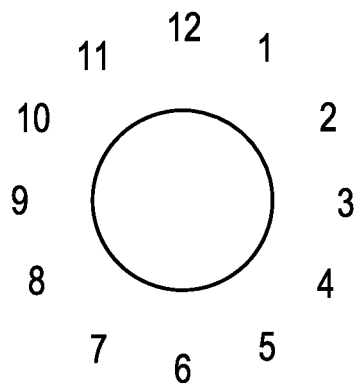
FIG. 15 is one embodiment of a syntax for expressing an indication of camera perspective.

An example method 1400 of a surgical procedure according to the present disclosure is shown in FIG. 14 and is described with reference to FIGS. 10-13. In an initial configuration, for example, a camera can be in the 6 o'clock position 1010, 1106 shown in FIGS. 10 and 11. The controller 208 can receive an output view from the camera (step 1402) and show the output view 1102 on the display 218, along with a camera position indicator 1106, 1108. A user can view the display 218 and recognize by either the temporary camera position indicator 1104 or the persistent camera position indicator 1108 (e.g., in a case where the temporary camera position indicator is not displayed) that their perspective is not aligned with the position of the camera. This can help the user address any confusion regarding the displayed view 1102 of the surgical site.

To better align the displayed output view of the camera to the user perspective, a user can directly manipulate the access device 102 and/or camera 202 into a new position. For example, the user can rotate the access device 102 and/or camera 202 180 degrees from the 6 o'clock position to the 12 o'clock position shown in FIGS. 12 and 13. In connection with moving the access device 102 and/or camera 202, the user can directly enter the new camera position using an interface, e.g., the display 1006 on the controller 208, by pressing the new camera position on the representation 1008 of the display 1006. Alternatively, if the controller 208 is more remotely located from the user and manned by a second user, e.g., an assistant, the user can call out the new camera position using the syntax or common language of the clock face and the second user can input this new position using the controller interface. As mentioned above, other input interfaces (e.g., a remote control, etc.) can be utilized as well. In this manner, the controller 208 can receive an input of camera position (step 1404).

Upon receiving the input or indication of camera position, the controller 208 can show on the display the output view of the camera and an indication of camera position based on the received input of camera position (step 1406). The indication of camera position can be an updated version of the persistent camera position indicator 1108 to show the new position, as shown in FIG. 13. In addition, the camera position indicator 1008 of the controller display 1006 can similarly be updated. Finally, to emphasize that a change of camera position has been entered, the more prominent temporary camera position indicator 1104 can be updated and shown on the screen (see FIG. 13) to highlight to a user viewing the display that a change has been registered. The temporary camera position indicator 1104 can be displayed for a finite period of time (e.g., in comparison to the constantly-displayed persistent camera position indicator 1108) to avoid distracting from the displayed camera output view. The finite period of time can be, e.g., between about 1 second and about 1 minute. In some embodiments, the finite period of time can be between about 1 second and about 10 seconds. In addition to the above-described feedback, other feedback can issue to a user, such as sounds, haptic feedback, other visual feedback, etc.

In some embodiments, the camera can be repositioned multiple times during a procedure as a user moves about the patient and adjusts the camera position accordingly. In such cases, the above-described procedure can be repeated with each move to update the camera position indicator displayed along with the output view of the camera. For example, a controller can receive a second input of camera position (step 1408) from a user and can show on the display the output view of the camera and an updated indication of camera position (step 1410).

Moreover, in some embodiments a user might wish to perform a transformation (e.g., rotation, inversion, etc.) of the displayed output view 1102 of the camera without physically moving the access device 102 and/or camera 202. Such transformations can be implemented by the controller 208 using software and can be controlled using the display 1006 on the controller or other interface. For example, the controller 208 can receive a desired transformation of the output view showed on the display based on a user perspective of the surgical site (step 1412). The controller 208 can show on the display a transformed output view from the camera based on the desired transformation and an updated indication of camera position reflecting the desired transformation (step 1414). This can include, for example, updating the camera position indicator to simulate a new position of the camera, adding a transformation label or a graphic representing the transformation, displaying a second indicator separate from the camera position indicator, etc.

Figure 16:
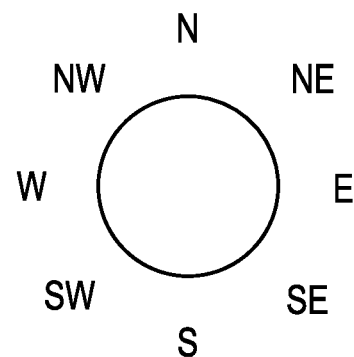
FIG. 16 is one embodiment of a syntax for expressing an indication of camera perspective.
Figure 17:
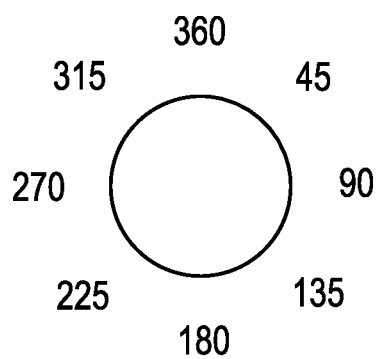
FIG. 17 is one embodiment of a syntax for expressing an indication of camera perspective.
Figure 18:
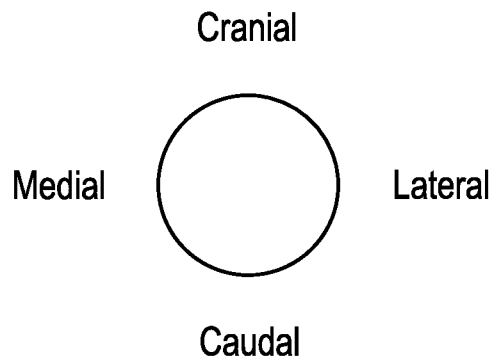
FIG. 18 is one embodiment of a syntax for expressing an indication of camera perspective.
Figures 19, 20:
FIG. 19 is one embodiment of a syntax for expressing an indication of camera perspective.
FIG. 20 is one embodiment of a syntax for expressing an indication of camera perspective.

While the above-described embodiments have utilized a representative syntax based on the face of a clock, a variety of other syntaxes are also possible, including any of a variety of syntaxes that equate positions around a circle with a common language that can be used to visually represent position and communicate adjustments thereto. FIGS. 15-23 illustrate various example syntaxes that can also be employed. These include the clock-face numerical sequence of FIG. 15, or any other numerical sequence. For example, FIG. 17 illustrates a numerical sequence of degrees of a circle akin to a compass. The cardinal compass directions, e.g., North, South, West, East, etc., can also be employed, as shown in FIG. 16. In some embodiments, anatomical terms of location, e.g., cranial, caudal, medial, lateral, etc., can be employed, as shown in FIG. 18. Other terms of location can also be employed, e.g., top, bottom, left, right, as shown in FIG. 19. In certain embodiments, directions can be indicated based on quadrants, sextants, octants, etc., as shown by the four-quadrant division of FIG. 20.

Figures 21, 22:
FIG. 21 is one embodiment of a syntax for expressing an indication of camera perspective.
FIG. 22 is one embodiment of a syntax for expressing an indication of camera perspective.
Figure 23:
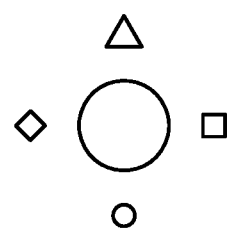
FIG. 23 is one embodiment of a syntax for expressing an indication of camera perspective.

Still other syntaxes are possible as well. For example, FIG. 21 illustrates a syntax based on a color wheel, where different directions can be expressed by different colors or names of colors. Analogous to numeric sequences, alphabetic or alphanumeric sequences can be utilized as well in some embodiments. FIG. 22, for example, illustrates an example alphabetic sequence to express direction or view orientation. FIG. 23 illustrates a further representative syntax based on shape matching, e.g., a triangle, square or rectangle, circle, diamond, etc., can each represent different directions or view orientations.

The above-described embodiments provide a representative syntax to aid a user in identifying a camera position from an indication according to the syntax, and for a user to communicate a new or desired camera position to another user and/or a controller or other system component using the syntax. In some embodiments, however, the systems and methods disclosed herein can also include one or more sensors that detect a position of the access tube 102 and/or camera 202 and automatically communicate the detected position with the controller 208 to update a camera position indicator displayed to a user in connection with, e.g., the controller 208 interface display 1006 or the camera position indicators 1008, 1104, 1108 shown on the display 218.

As noted above and shown in FIG. 2, the access device 102 and/or camera 202 can include one or more sensors 222 capable of detecting a position thereof. The sensor 222 can be a magnetic sensor, an optical sensor, a laser sensor, an electronic sensor, or any other type of sensor that can be configured to detect a position of the access port 102 and/or camera 202 relative to, e.g., an axis of the access device 102.

In some embodiments, a user can position an access port in an initial desired configuration and designate the camera position in the manner described above, e.g., by designating the camera in a particular position around a circle according to a clock face reading, etc. Further, the initial designation can align with a user's direct perspective in the operating environment. After receiving the initial camera position indication, the one or more sensors 222 can be utilized to track any subsequent movement of the access port 102 and/or camera 202 and communicate such movements to the controller 208. The controller 208 can automatically adjust the camera position indicator based on the received information from the one or more sensors 222 without requiring separate inputs of new camera positions via, e.g., the display 1006 as described above. Further, in some embodiments various transformations (e.g., rotations, etc.) can be performed based on the movements of the access device 102 and/or camera 202 to keep the displayed output view aligned with the initial camera position indication provided by the user that corresponds to the user's direct perspective in the operating room. The camera position indicator can be updated to reflect such transformations as described above, e.g., by providing a separate indication of a transformation, incorporating the transformation into the camera position indication, etc. For example, in one embodiment a camera position indicator might note that the camera is at a 6 o'clock position but the displayed output view is rotated 180 degrees to simulate a view from a 12 o'clock position.

In other embodiments, a user can designate their perspective directly using any of the syntaxes disclosed herein (e.g., as a clock-face reading, cardinal direction reading, etc.). The controller 208 can track any movement of the access device 102 and/or camera 202 relative to this perspective and update the camera position indicator to express any changes. Alternatively or in addition, the controller 208 can implement any of a variety of transformations of the displayed output view to keep the displayed output view aligned with the user perspective.

In still other embodiments, the access device 102 can include a perspective indicator 304, as shown in FIG. 3, that can be coupled to a proximal end of the access device and configured to move about a circumference thereof. The perspective indicator 304 can be positioned by a user after placing the access port in order to indicate their physical position. The perspective indicator 304 can include a sensor or otherwise be coupled to a sensor that can detect the position of the perspective indicator about the circumference of the access device 102 and communicate it to the controller 208. The controller 208 can utilize the position of the perspective indicator 304 to update the displayed camera position indicator and/or output view, as well as to track any future movement of the access device, camera, and/or perspective indicator and update a displayed camera position indicator and/or displayed camera output view accordingly.

The instruments disclosed herein can be constructed from any of a variety of known materials. Such materials include those which are suitable for use in surgical applications, including metals such as stainless steel, titanium, nickel, cobalt-chromium, or alloys and combinations thereof, polymers such as PEEK, carbon fiber, and so forth. The various components of the instruments disclosed herein can have varying degrees of rigidity or flexibility, as appropriate for their use. Device sizes can also vary greatly, depending on the intended use and surgical site anatomy. Furthermore, particular components can be formed from a different material than other components. One or more components or portions of the instrument can be formed from a radiopaque material to facilitate visualization under fluoroscopy and other imaging techniques, or from a radiolucent material, such as carbon fiber and/or high-strength polymers, so as not to interfere with visualization of other structures.

The devices, systems, and methods disclosed herein can be used in minimally-invasive surgery and/or open surgery. While the devices, systems, and methods disclosed herein are generally described in the context of surgery on a human patient, it will be appreciated that the devices, systems, and methods disclosed herein can be used in any of a variety of surgical procedures with any human or animal subject, or in non-surgical procedures.

The devices, systems, and methods disclosed herein can be designed to be disposed of after a single use, or they can be designed to be used multiple times. In either case, however, certain components can be reconditioned for reuse after at least one use. Reconditioning can include any combination of the steps of disassembly, cleaning or replacement of particular components, and subsequent reassembly. In particular, a component can be disassembled, and any number of the particular pieces or parts of the component can be selectively replaced or removed in any combination. Upon cleaning and/or replacement of particular parts, the component can be reassembled for subsequent use either at a reconditioning facility, or by a surgical team immediately prior to a surgical procedure. Reconditioning of a device can utilize a variety of techniques for disassembly, cleaning/replacement, and reassembly. Use of such techniques, and the resulting reconditioned component, are all within the scope of the present disclosure.

Although specific embodiments are described above, changes may be made within the spirit and scope of the concepts described. For example, while certain components disclosed herein are generally described as operable by hand, in some embodiments, these components can be operated, for example, by a robot, etc. Accordingly, it is intended that this disclosure not be limited to the described embodiments, but that it have the full scope defined by the language of the claims. All publications and references cited herein are expressly incorporated by reference in their entirety.

The invention claimed is:

1. A surgical method, comprising:
   receiving an output view from a camera placed within a channel of an access device to view a surgical site within a patient;
   receiving a first input of camera position around a central longitudinal axis of the access device from a sensor;
   showing on a display the output view from the camera and a graphical indication of camera position around the central longitudinal axis of the access device based on the first input of camera position;
   rotating the camera around the central longitudinal axis of the access device while showing on the display the output view from the camera and the graphical indication of camera position;
   receiving a second input of camera position from the sensor after rotating the camera; and
   showing on the display an updated indication of camera position around the central longitudinal axis of the access device based on the second input of camera position.

2. The method of claim 1, wherein the display includes an augmented reality display.

3. The method of claim 1, wherein the input is received at a second display.

4. The method of claim 3, wherein the second display shows the indication of camera position.

5. The method of claim 4, wherein the second display shows the indication of camera position constantly and the display shows the indication of camera position temporarily in connection with receiving any of the first or second inputs of camera position.

6. The method of claim 1, wherein the indication of camera position is shown temporarily in connection with receiving any of the first or second inputs of camera position.

7. The method of claim 1, wherein the indication of camera position is shown persistently.

8. The method of claim 1, wherein the indication of camera position is any of a clock reading, a compass reading, a cardinal body direction, a circle degree reading, a quadrant, a spatial direction, a color, a reading from an alphabetic sequence, a reading from a numerical sequence, or a reading from a shape sequence.

9. The method of claim 1, further comprising:
   receiving from a user a desired transformation of the output view showed on the display based on a user perspective of the surgical site;
   showing on the display a transformed output view from the camera based on the desired transformation and a second indication reflecting the desired transformation in addition to the indication of camera position.

10. The method of claim 1, further comprising designating an initial position of the camera around the central longitudinal axis of the access device, wherein the sensor is configured to track subsequent movement of the camera around the central longitudinal axis of the access device relative to the initial position.

11. The method of claim 1, further comprising
    receiving an input of a user position around a circumference of the access device from a perspective indicator coupled to a proximal end of the access device and configured to move about a circumference thereof; and
    transforming the output view shown on the display based on the input of user position.

12. A surgical system, comprising:
    an access device configured to provide a working channel to a surgical site within a patient;
    a camera configured to be disposed within the access device radially outward from a central longitudinal axis of the working channel to view the surgical site;
    a sensor coupled to the access device;
    a display; and
    a controller configured to:
      receive an output view from the camera;
      receive an input of camera position around the central longitudinal axis of the working channel from the sensor; and
      show on the display the output view from the camera and a graphical indication of camera position around the central longitudinal axis of the working channel based on the input of camera position.

13. The system of claim 12, wherein the display includes an augmented reality display.

14. The system of claim 12, further comprising a second display configured to receive the input.

15. The system of claim 14, wherein the controller is further configured to show the indication of camera position on the second display.

16. The system of claim 15, wherein the controller is further configured to show the indication of camera position constantly on the second display and show the indication of camera position on the display temporarily in connection with receiving the input of camera position.

17. The system of claim 12, wherein the controller is further configured to show the indication of camera position temporarily in connection with receiving the input of camera position.

18. The system of claim 12, wherein the controller is further configured to show the indication of camera position persistently on the display.

19. The system of claim 12, wherein the controller is further configured to show the indication of camera position as any of a clock reading, a compass reading, a cardinal body direction, a circle degree reading, a quadrant, a spatial direction, a color, a reading from an alphabetic sequence, a reading from a numerical sequence, or a reading from a shape sequence.

20. The system of claim 12, wherein the controller is further configured to:
   receive a second input of camera position from the sensor based on movement of the camera; and
   show on the display an updated indication of camera position based on the second input of camera position while continuously showing the output view from the camera.

21. The system of claim 12, wherein the controller is further configured to:
   receive a desired transformation of the output view showed on the display based on a user perspective of the surgical site;
   show on the display a transformed output view from the camera based on the desired transformation and a second indication reflecting the desired transformation in addition to the indication of camera position.

22. The system of claim 12, further comprising a perspective indicator coupled to a proximal end of the access device and configured to move about a circumference thereof to communicate a position of the user around the circumference of the access device to the controller;
   wherein the controller is configured to transform the output view based on the position of the user.

* * * * *